US009357945B2

(12) United States Patent
Akimoto et al.

(10) Patent No.: US 9,357,945 B2
(45) Date of Patent: Jun. 7, 2016

(54) ENDOSCOPE SYSTEM HAVING A POSITION AND POSTURE CALCULATING PORTION

(71) Applicant: OLYMPUS CORPORATION, Tokyo (JP)

(72) Inventors: Syunya Akimoto, Kawasaki (JP); Junichi Onishi, Hachioji (JP); Mitsuhiro Ito, Akiruno (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/670,858

(22) Filed: Mar. 27, 2015

(65) Prior Publication Data

US 2015/0196228 A1 Jul. 16, 2015

Related U.S. Application Data

(63) Continuation of application No. PCT/JP2014/060398, filed on Apr. 10, 2014.

(30) Foreign Application Priority Data

Apr. 15, 2013 (JP) ................................. 2013-084918

(51) Int. Cl.
*A61B 1/04* (2006.01)
*A61B 1/00* (2006.01)
(Continued)

(52) U.S. Cl.
CPC ............. *A61B 5/065* (2013.01); *A61B 1/00009* (2013.01); *A61B 1/00147* (2013.01);
(Continued)

(58) Field of Classification Search
CPC ........ A61B 1/00009; A61B 1/05; A61B 1/06; A61B 5/065; A61B 5/061; A61B 19/5225; A61B 2019/5231; A61B 2019/5265; A61B 2019/5291
See application file for complete search history.

(56) References Cited

U.S. PATENT DOCUMENTS

2007/0103464 A1* 5/2007 Kaufman ............. G06T 7/0012
345/424
2009/0292166 A1 11/2009 Ito et al.
(Continued)

FOREIGN PATENT DOCUMENTS

EP 1 543 765 A1 6/2005
EP 1 917 901 A1 5/2008
(Continued)

OTHER PUBLICATIONS

International Search Report dated Jul. 8, 2014 issued in PCT/JP2014/060398.
(Continued)

*Primary Examiner* — John P Leubecker
(74) *Attorney, Agent, or Firm* — Scully, Scott, Murphy & Presser, P.C.

(57) ABSTRACT

An endoscope system includes: a position and posture calculating portion that estimates a position of a distal end and a longitudinal direction of a distal end portion; a condition determining portion that, based on the shape information at the position of the distal end that is estimated, determines whether or not an angle that a core line direction of the luminal organ and the longitudinal direction estimated by the position and posture calculating portion form is equal to or less than a predetermined threshold value; and a position and posture information recording portion that, when the angle that the core line direction and the longitudinal direction form is equal to or less than the predetermined threshold value, records information regarding the position and the longitudinal direction of the distal end.

11 Claims, 13 Drawing Sheets

(51) Int. Cl.
  *A61B 5/06* (2006.01)
  *A61B 19/00* (2006.01)
  *A61B 1/05* (2006.01)
  *A61B 1/06* (2006.01)

(52) U.S. Cl.
  CPC .. *A61B 1/05* (2013.01); *A61B 1/06* (2013.01); *A61B 5/061* (2013.01); *A61B 19/5225* (2013.01); *A61B 2019/5231* (2013.01); *A61B 2019/5265* (2013.01); *A61B 2019/5291* (2013.01)

(56) References Cited

U.S. PATENT DOCUMENTS

| | | | | |
|---|---|---|---|---|
| 2010/0201683 | A1* | 8/2010 | Shirahata | G06F 19/321 345/420 |
| 2010/0220917 | A1* | 9/2010 | Steinberg | G06T 7/0022 382/134 |
| 2011/0018871 | A1* | 1/2011 | Shirahata | A61B 8/00 345/419 |
| 2011/0184238 | A1* | 7/2011 | Higgins | A61B 1/00009 600/117 |
| 2011/0234780 | A1 | 9/2011 | Ito et al. | |
| 2012/0287238 | A1* | 11/2012 | Onishi | A61B 1/0005 348/45 |

FOREIGN PATENT DOCUMENTS

| | | |
|---|---|---|
| EP | 2123216 A1 | 11/2009 |
| EP | 2377457 A1 | 10/2011 |
| JP | 2003-265408 A | 9/2003 |
| JP | 2009-279250 A | 12/2009 |
| JP | 4728456 B1 | 7/2011 |
| JP | 2011-189074 A | 9/2011 |
| JP | 2012-024518 A | 2/2012 |
| WO | WO 2011/102012 A1 | 8/2011 |
| WO | WO 2013/031637 A1 | 3/2013 |

OTHER PUBLICATIONS

Extended Supplementary European Search Report dated Apr. 19, 2016 from related European Application No. 14 78 5125.7

* cited by examiner

ENDOSCOPE SYSTEM HAVING A POSITION AND POSTURE CALCULATING PORTION

CROSS REFERENCE TO RELATED APPLICATION

This application is a continuation application of PCT/JP2014/060398 filed on Apr. 10, 2014 and claims benefit of Japanese Application No. 2013-084918 filed in Japan on Apr. 15, 2013, the entire contents of which are incorporated herein by this reference.

BACKGROUND OF THE INVENTION

1. Field of the Invention

The present invention relates to an endoscope system that picks up an image of inside a subject using image pickup means.

2. Description of the Related Art

In recent years, an endoscope having an insertion portion that is insertable into a body cavity or the like has been widely used in medical fields and the like.

In the case of inserting the insertion portion into a luminal organ that branches in a complicated manner, such as bronchial tubes, within a body cavity to inspect (diseased tissue at) a target site at a distal end side of the luminal organ or to perform a biopsy or treatment using a treatment instrument, it is sometimes difficult to introduce the distal end of the insertion portion as far as the vicinity of the target site using only an endoscopic image that is obtained when the insertion portion is inserted.

Therefore, systems or apparatuses have been proposed that display images to support an operation to introduce the distal end of the insertion portion of an endoscope as far as the vicinity of a target site.

For example, as a first conventional example, Japanese Patent Application Laid-Open Publication No. 2011-189074 discloses a medical apparatus that includes: an insertion portion to be inserted into the bronchial tubes; a plurality of FBG sensor portions that are arranged in the insertion portion; a storage portion for storing previously acquired three-dimensional image data of the bronchial tubes; a shape measurement portion for measuring a shape of the insertion portion based on data of the FBG sensor portions; a core line calculating portion for calculating a core line of the bronchial tubes based on three-dimensional image data stored in the storage portion; and a position calculating portion for calculating a position of the insertion portion based on the shape that is measured by the shape measurement portion and the core line that is calculated by the core line calculating portion. The medical apparatus calculates a position and a direction of the distal end of the insertion portion by extracting the core line.

Further, as a second conventional example, Japanese Patent Application Laid-Open Publication No. 2012-24518 discloses a support apparatus that: acquires a central line of a tubular tissue (tubular organ) of a subject from a previously acquired three-dimensional image of the subject; displays an endoscopic image that was photographed while moving an endoscope that was inserted into the tubular tissue along the longitudinal direction of the tubular tissue; inputs a reference position of the endoscope at a time at which one feature region of the tubular tissue is shown in the displayed endoscopic image, and also sets a position corresponding to the one feature region on the central line; acquires a movement amount and a travelling direction of the endoscope when the endoscope has moved from the reference position; calculates a position that is at a distance corresponding to the acquired movement amount in the acquired travelling direction along the central line from the position corresponding to the one feature region as a current position; and displays an indicator representing the calculated current position on the central line. The support apparatus further calculates the position of image pickup means based on the core line of the tubular organ and a movement amount and a travelling direction of the image pickup means.

The aforementioned first conventional example discloses technology that is based on the viewpoint of calculating a position of a distal end of an insertion portion by extracting a core line, while the second conventional example discloses calculating the position of image pickup means (endoscope distal end) by means of a core line of a luminal organ and a movement amount and travelling direction of the image pickup means (endoscope distal end).

SUMMARY OF THE INVENTION

An endoscope system according to one aspect of the present invention is an endoscope system capable of previously acquiring shape information that is associated with positional information regarding a luminal organ of a subject, the endoscope system including: a position and posture calculating portion that estimates a position of a distal end of an endoscope insertion portion and a longitudinal direction of a distal end portion of the endoscope insertion portion; a condition determining portion that, based on the shape information at a position of the distal end of the endoscope insertion portion estimated by the position and posture calculating portion, determines whether or not an angle that a core line direction of a core line that is positioned at approximately a center of the luminal organ and a longitudinal direction of the distal end portion of the endoscope insertion portion that is estimated by the position and posture calculating portion is equal to or less than a predetermined threshold value; and a position and posture information recording portion configured to, in a case where an angle that the core line direction and the longitudinal direction of the distal end portion of the endoscope insertion portion form is equal to or less than a predetermined threshold value, record information regarding the position of the distal end of the endoscope insertion portion and the longitudinal direction of the distal end portion of the endoscope insertion portion that is estimated by the position and posture calculating portion.

DETAILED DESCRIPTION OF THE PREFERRED EMBODIMENTS

Hereunder, embodiments of the present invention are described with reference to the drawings.

First Embodiment

Figure 1:
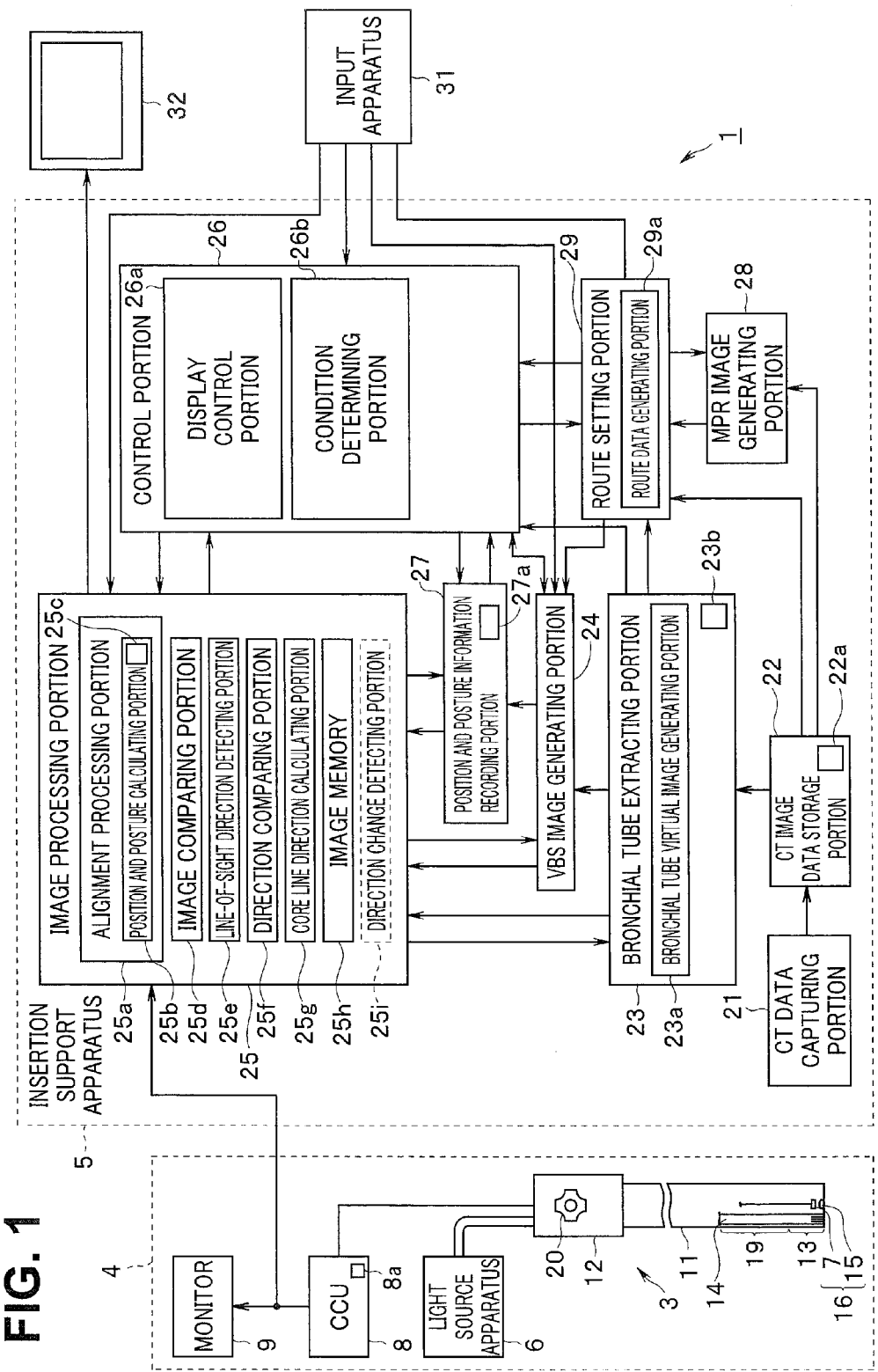
FIG. 1 is a view illustrating the overall configuration of an endoscope system according to a first embodiment of the present invention.

As shown in FIG. 1, an endoscope system 1 according to a first embodiment of the present invention is mainly constituted by an endoscope apparatus 4 including an endoscope 3 to be inserted into bronchial tubes 2 (see FIG. 2A) as a predetermined luminal organ in a patient that is a subject to be examined, and an insertion support apparatus 5 that is used together with the endoscope apparatus 4 to support insertion of the endoscope 3.

The endoscope apparatus 4 includes the endoscope 3, a light source apparatus 6 for supplying illumination light to the endoscope 3, a camera control unit (abbreviated as "CCU") 8 as a signal processing apparatus for performing signal processing with respect to an image pickup device 7 which is mounted in the endoscope 3 and which constitutes image pickup means (image pickup portion), and a monitor 9 as a display apparatus (display portion) for displaying an endoscopic image generated by the CCU 8.

The endoscope 3 includes an elongated insertion portion (also referred to as "endoscope insertion portion") 11 having flexibility, an operation portion 12 provided at a rear end of the insertion portion 11, and an illuminating window and an observation window that are provided in a distal end portion 13 provided in the vicinity of a distal end of the insertion portion 11. A light guide 14 that transmits illuminating light is inserted through the inside of the insertion portion 11 and operation portion 12. An incident end of a rear end of the light guide 14 is connected to the light source apparatus 6, and illuminating light generated by an unshown light source lamp or LED inside the light source apparatus 6 is incident on the incident end. The illuminating light transmitted by the light guide 14 is emitted in the forward direction from an emitting end (distal end face) attached to the illuminating window.

An objective lens 15 forming an objective optical system that forms an image of an object is attached to the observation window, and the image pickup device 7 such as a charge-coupled device (CCD) is disposed at the image forming position. An image pickup apparatus 16 as image pickup means (an image pickup portion) that picks up, as an object, an image of the inside of the bronchial tubes 2 as a predetermined luminal organ into which the insertion portion 11 is inserted is formed by the objective lens 15 and the image pickup device 7.

Note that, in the present embodiment, the optical axis direction of the objective lens 15 is parallel to the axial direction or longitudinal direction of the distal end portion 13 (or distal end) of the insertion portion 11. Accordingly, an image pickup direction in which an image of an object is picked up by the image pickup apparatus 16 (or a line-of-sight direction in which a user looks through the image pickup apparatus 16) is the direction towards the front side (opposite side to the image pickup device 7) of the objective lens 15 along the optical axis direction of the objective lens 15. Further, it can be approximated that the optical axis direction of the objective lens 15 and the axial direction or longitudinal direction of the distal end portion 13 of the insertion portion 11 are matching.

Consequently, in the present embodiment, it can be approximated that the image pickup direction or the line-of-sight direction of the image pickup device 7 through the objective lens 15 matches the axial direction or longitudinal direction of the distal end of the insertion portion 11. Further, the position and posture of the distal end of the insertion portion 11 are determined based on at least information regarding the image pickup direction or line-of-sight direction of the objective lens 15 that is disposed in the distal end of the insertion portion 11, and conversely, the image pickup direction or line-of-sight direction of the objective lens 15 is determined based on information regarding the position and posture of the distal end of the insertion portion 11.

In the present embodiment, the position and posture of the distal end of the insertion portion 11 can also be referred to in another way as the position of the distal end of the insertion portion 11 and the axial direction or longitudinal direction of the distal end or the line-of-sight direction of the objective lens 15.

Note that the present invention is not limited to the endoscope 3 having a configuration in which the image pickup apparatus 16 is provided in the distal end portion 13 as shown in FIG. 1, and can also be applied to a fiberscope in which the distal end face of an image guide constituted by a fiber bundle is disposed at an image forming position of the objective lens 15 that is provided in the distal end portion 13, and to a camera-mounted endoscope in which a TV camera is mounted at an ocular portion of the aforementioned image guide. In both of these endoscopes, at least the objective lens 15 is disposed in the distal end portion 13. Therefore, the line-of-sight direction of the objective lens 15 or a line-of-sight direction that is obtained by means of the objective lens 15 is mainly used rather than the line-of-sight direction of the image pickup apparatus 16.

The image pickup device 7 is connected to the CCU 8 through a signal line inserted through the insertion portion 11 and the operation portion 12. By means of an image signal generating circuit 8a provided therein, the CCU 8 generates an image signal of a picked-up image corresponding to an optical image formed on an image pickup surface of the image pickup device 7, and outputs the image signal to the monitor 9. The monitor 9 displays an image (movie) in accordance with the image signal as an endoscopic image.

A bending portion 19 that is bendable is provided at a rear end of the distal end portion 13 in the insertion portion 11 of the endoscope 3. A surgeon can bend the bending portion 19 in arbitrary directions among the upward, downward, right and left directions via unshown wires by performing an operation to rotate a bending operation knob 20 that is provided on the operation portion 12.

The insertion support apparatus 5 includes a CT data capturing portion 21 that, with respect to a patient who is undergoing an examination using the endoscope 3, captures CT data as three-dimensional image information of the patient which was generated by a known CT apparatus through a portable storage medium such as a DVD, a Blu-ray Disc or a flash memory, and a CT image data storage portion 22 that stores the CT data captured by the CT data capturing portion 21.

Note that the CT image data storage portion 22 may also store the CT data (as three-dimensional image information of the patient as a subject) that was generated by the CT apparatus via a communication line, the Internet, or the like. The CT image data storage portion 22 can be constituted by a hard disc device, a flash memory, a DVD, or the like.

Further, the CT image data storage portion 22 constituting image storage means includes an associated image information storage portion 22a that stores associated image information that is obtained by associating CT image data that was obtained by separating image data from CT data with three-dimensional position data using a first coordinate system that corresponds to the CT image data that was obtained by separating positional information from CT data.

Furthermore, the insertion support apparatus 5 includes a bronchial tube extracting portion 23 constituted by a luminal organ extracting circuit or the like as luminal organ extracting means for extracting three-dimensional image data of the bronchial tubes 2 as a predetermined luminal organ from the CT image data in the CT image data storage portion 22.

Based on the extracted three-dimensional data (more specifically, three-dimensional volume data) of the bronchial tubes 2, the bronchial tube extracting portion 23 generates information of a three-dimensional shape (shape data) which represents a hollow shape of the bronchial tubes 2 and image information (image data) of a three-dimensional shape. That is, the bronchial tube extracting portion 23 includes a bronchial tube shape image generating portion 23a as bronchial tube shape image generating means for generating a bronchial tube shape image as an image of a hollow three-dimensional bronchial tube shape based on the extracted three-dimensional image data of the bronchial tubes 2. Note that the bronchial tube extracting portion 23 may be constituted by software of a central processing unit (abbreviated as "CPU") or the like, or may be constituted by hardware using an FPGA (field programmable gate array) or electronic circuit elements or the like. Note that, an image processing portion 25 and a control portion 26 that are described later may also be constituted by software of a CPU or the like, or may be constituted by hardware using an FPGA or electronic circuit elements.

When extracting the three-dimensional data of the bronchial tubes 2, the bronchial tube extracting portion 23 extracts the three-dimensional data in association with three-dimensional position data of the first coordinate system (or CT coordinate system) that corresponds to the three-dimensional data. The bronchial tube extracting portion 23 also has an associated information storage portion 23b constituted by a memory or the like that stores associated information in which data of the three-dimensional shape of the bronchial tubes 2 (that is, bronchial tube shape data) and three-dimensional position data are associated.

The insertion support apparatus 5 includes a VBS image generating portion 24 constituted by a VBS image generating circuit that forms virtual endoscopic image generating means for generating a virtual endoscopic image (referred to as "VBS image") as a virtual endoscopic image that corresponds to an endoscopic image that is picked up by the image pickup device 7 through the objective lens 15 provided in the distal end portion 13 of the insertion portion 11 in the endoscope 3.

Information relating to the objective lens 15 and image pickup device 7 mounted in the distal end portion 13 of the endoscope 3 (information such as the focal distance of the objective lens 15 and the number of pixels and image size of the image pickup device 7) is inputted to the VBS image generating portion 24 from, for example, an input apparatus 31.

Based on characteristics information of an image forming system that forms an image of an object inside the bronchial tubes 2 on the image pickup surface of the image pickup device 7 by means of the objective lens 15 disposed at the distal end of the endoscope 3 that has been actually inserted into the bronchial tubes 2, information such as the pixel size and number of pixels of the image pickup device 7 that converts an optical image formed on the image pickup surface into an endoscopic image, and bronchial tube shape data, the VBS image generating portion 24 generates a VBS image by virtually rendering an endoscopic image obtained by endoscopically picking up an image of the inside of the bronchial tubes 2 along the line-of-sight direction of the objective lens 15 in a manner in which a three-dimensional position in the CT coordinate system (also referred to simply as "position") of the distal end of the insertion portion 11 of the endoscope 3 that has been inserted into the bronchial tubes 2 is taken as the viewing point position.

That is, as a VBS image, the VBS image generating portion 24 generates an image of the inside of the bronchial tubes 2 that is formed on the image pickup surface of the image pickup device 7 by taking the position of the (objective lens 15 of the) distal end of the insertion portion 11 in the CT coordinate system as the viewing point position, and on the basis that the objective lens 15 at the viewing point position is virtually disposed so that the optical axis thereof is along the line-of-sight direction and the image pickup surface of the image pickup device 7 is virtually disposed at the image forming position thereof.

Accordingly, in a state in which the endoscopic image and the VBS image have been subjected to image matching so that the two images sufficiently match, information regarding the position of the distal end of the insertion portion 11 of the endoscope 3 and regarding the posture in the longitudinal direction of the distal end that practically matches the line-of-sight direction of the objective lens 15 that is disposed in the distal end can be acquired based on information regarding the viewing point position and the line-of-sight direction with respect to the VBS image in the CT coordinate system. A position and posture calculating portion 25b that is described later calculates (estimates) position and posture information in this way.

Note that, in a case where the endoscope 3 includes an identification information generating portion that is constituted by a ROM or the like that generates unique identification information for each endoscope 3, the VBS image generating portion 24 may be configured to automatically acquire information regarding the objective lens 15 and the image pickup device 7 mounted in the relevant endoscope 3 based on identification information of the endoscope 3 that is connected to the insertion support apparatus 5, and generate a corresponding VBS image.

Further, the insertion support apparatus 5 includes: an image processing portion 25 configured to perform image processing such as image processing of an alignment processing portion 25a that is configured to perform, by image matching, alignment between an endoscopic image inputted from the CCU 8 and a VBS image of the VBS image generating portion 24; the control portion 26 as control means configured to perform control of the image processing portion 25 and the like; and a position and posture information recording portion 27 as position and posture information recording means configured to record information regarding the position and posture of the distal end of the insertion portion 11 that is utilized as information for supporting insertion under control of the control portion 26. Note that, in the present embodiment, the posture of the distal end of the insertion portion 11 is determined based on the longitudinal direction or axial direction of the distal end (that practically matches the line-of-sight direction of the objective lens 15 disposed in the distal end).

The insertion support apparatus 5 also includes an MPR image generating portion 28 that is configured to generate a CT tomogram (referred to as an "MPR image") as a multi-planar reconstruction image based on the CT image data stored in the CT image data storage portion 22, and a route setting portion 29 configured to generate a route setting screen as a screen for setting an insertion route that has an MPR image generated by the MPR image generating portion 28 and to set a route to follow when inserting the endoscope 3 to the side of a target site inside the bronchial tubes 2.

Figure 2A:
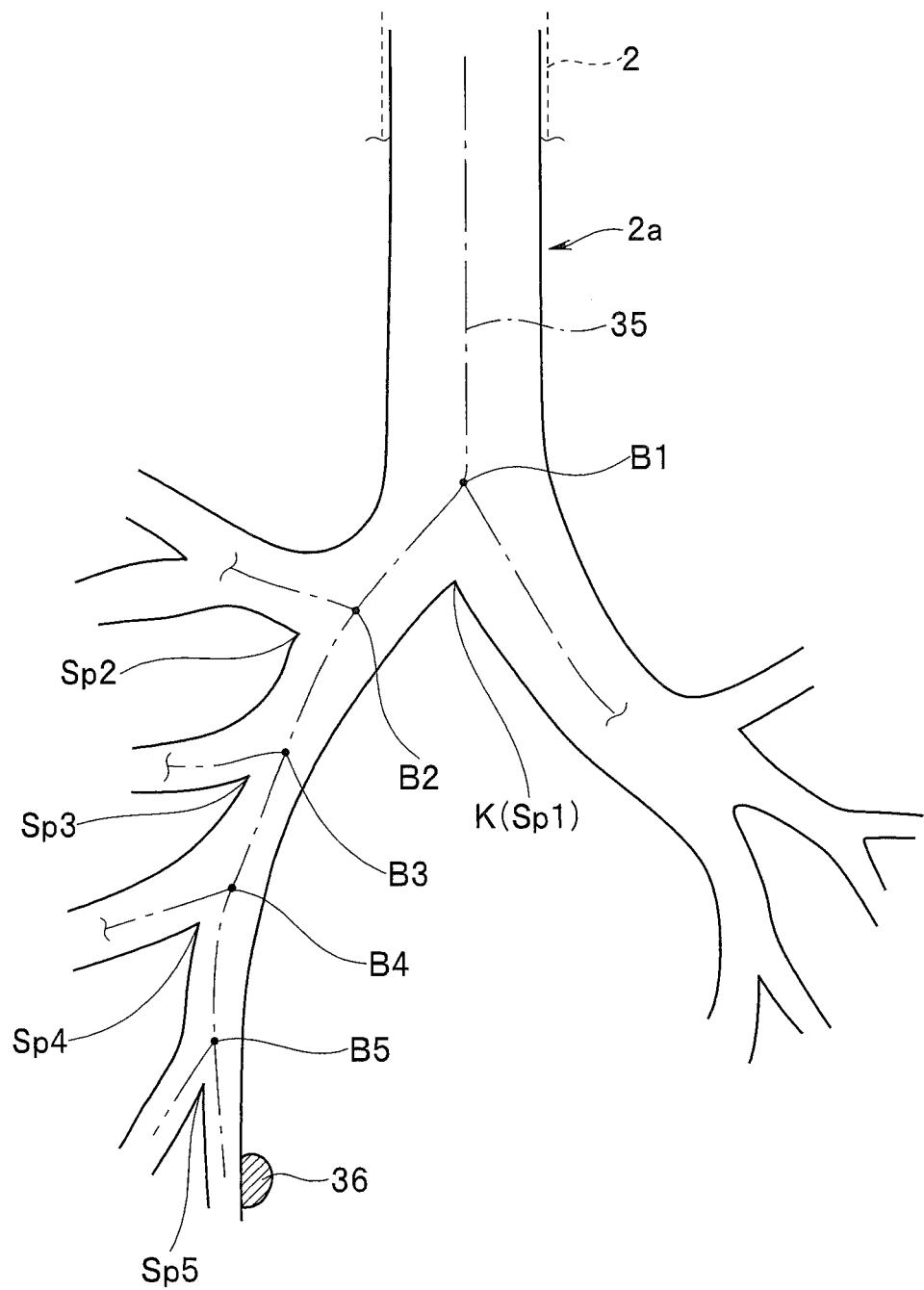
FIG. 2A is a view illustrating a bronchial tube shape image as a shape image of bronchial tubes.

Further, for example, in a case where a target site 36 as shown in FIG. 2A was designated based on the CT image data, the route setting portion 29 includes a function of a route data generating portion (or a route data generating circuit) 29a that generates route data for a route to a target position that is the vicinity of the target site 36 from an insertion starting position (of the insertion portion 11) in the bronchial tubes 2 based on the CT image data and a bronchial tube shape image 2a. Note that spurs Spi (i=1, 2, 3, 4, 5) that are boundaries in the bronchial tubes 2 at which the lumen branches into bronchial branches, and branch points Bi at which a core line 35 as the central line of the lumen branches are illustrated in FIG. 2A.

Further, the endoscope system 1 includes an input apparatus 31 constituted by a keyboard and a pointing device or the like for inputting setting information to the route setting portion 29. The surgeon can input parameters or data for a time of performing image processing from the input apparatus 31 to the image processing portion 25, and can also select or instruct a control operation with respect to the control portion 26.

In a case where the surgeon performed an operation to set a route, the route setting portion 29 sends information regarding the route that was set to the VBS image generating portion 24, the MPR image generating portion 28 and the control portion 26. The VBS image generating portion 24 and the MPR image generating portion 28 generate a VBS image and a MPR image along the route, respectively, and the control portion 26 performs control of the operations of each portion along the route.

An endoscopic image generated by the CCU 8 and a VBS image generated by the VBS image generating portion 24 are inputted to the image processing portion 25. The bronchial tube shape image 2a generated by the bronchial tube shape image generating portion 23a is also inputted to the image processing portion 25.

In the present embodiment, since a sensor for detecting the position of the distal end of the insertion portion 11 is not mounted in the distal end portion 13 of the insertion portion 11 in which the image pickup apparatus 16 is disposed, the alignment processing portion 25a of the image processing portion 25 estimates (or calculates) the position of the distal end of the insertion portion 11 and the longitudinal direction or axial direction of the distal end as the posture thereof by image matching. That is, the alignment processing portion 25a includes a function of a position and posture calculating portion (position and posture calculating circuit) 25b as position and posture calculating means for calculating information of the position and posture of the distal end of the insertion portion 11 by image matching.

More specifically, a three-dimensional position (position that is already known) that can be specified by the CT coordinate system from the bronchial tube shape image 2a, such as the entrance of the bronchial tubes 2 or the carina K (see FIG. 2A), or a position in the vicinity of the aforementioned positions is set in advance as a starting position for image matching, and the VBS image generating portion 24 generates a VBS image based on position and posture information thereof that was set in consideration of the line-of-sight direction and optical properties of the objective lens 15.

The surgeon then inserts the distal end of the insertion portion 11 so that the endoscopic image appears the same as the VBS image. Upon performing this alignment, the alignment processing portion 25a of the image processing portion 25 starts processing for image matching so that the endoscopic image and the VBS image match under a set condition (within the range of an error such that a predetermined accuracy can be secured). By performing such processing, the alignment processing portion 25a has a function of a position and posture calculating portion (position and posture calculating circuit) 25b as position and posture calculating means for detecting by estimation or calculating the position of the distal end of the insertion portion 11 and a posture that is determined based on the line-of-sight direction (or longitudinal direction of the distal end) of the objective lens 15.

Note that the position and posture calculating portion 25b includes a function of a position calculating portion (position calculating circuit) 25c as position calculating means for detecting by estimation or calculating a three-dimensional position of the distal end of the insertion portion 11.

Figure 4:
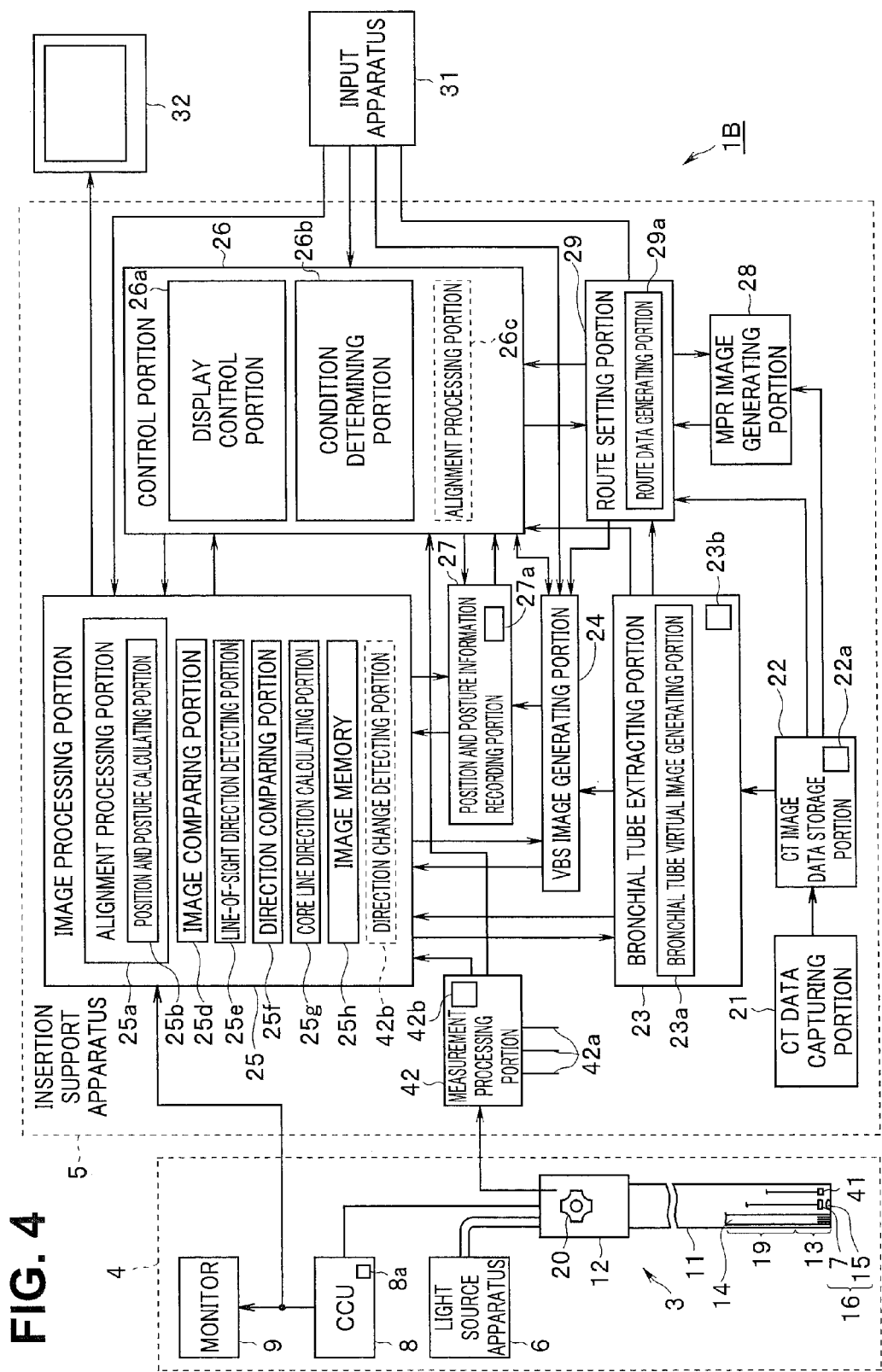
FIG. 4 is a view illustrating the overall configuration of an endoscope system according to a first modification of the first embodiment that includes a position sensor.

As described later in a modification that is illustrated in FIG. 4, a configuration may also be adopted in which a position sensor 41 for position detection is provided in the distal end portion 13, a position calculating portion 42b is provided that detects (calculates) the three-dimensional position of the distal end of the insertion portion 11 using the position sensor 41, and the posture is calculated by image matching. Note that, in the present specification, the term "distal end of the insertion portion 11" is used with the same meaning as "distal end of the endoscope 3".

Further, the image processing portion 25 includes: an image comparing portion (image comparing circuit) 25d as image comparing means for comparing an endoscopic image acquired by the image pickup device 7 through the objective lens 15 with a VBS image; a line-of-sight direction detecting portion (line-of-sight direction detecting circuit) 25e as line-of-sight direction detecting means for detecting a line-of-sight direction of the objective lens 15; and a direction comparing portion (direction comparing circuit) 25f as direction comparing means for comparing a core line direction as the direction of a central line of a lumen of the bronchial tubes 2 with the line-of-sight direction.

Furthermore, the image processing portion 25 includes a core line direction calculating portion (core line direction calculating circuit) 25g that calculates (acquires) a core line direction in the vicinity of the position of the distal end of the insertion portion 11 with respect to which the line-of-sight direction detecting portion 25e detected the line-of-sight direction. The core line direction calculating portion 25g, for example, calculates a tangent of the core line 35 in the CT coordinate system that corresponds to the vicinity of the position of the distal end of the insertion portion 11 with respect to which the line-of-sight direction detecting portion 25e detected the line-of-sight direction, or a direction that is close to the tangent, as the core line direction (at the time of comparison with the line-of-sight direction). The direction comparing portion 25f then compares the aforementioned line-of-sight direction and the core line direction calculated by the core line direction calculating portion 25g. The line-of-sight direction detecting portion 25e or the direction comparing portion 25f may also be configured to include the function of the core line direction calculating portion 25g. In a case where the direction comparing portion 25f is configured to include the function of the core line direction calculating portion 25g, the direction comparing portion 25f calculates the core line direction of the bronchial tubes as a predetermined luminal organ that is extracted by the bronchial tube extracting portion 23 constituting a luminal organ extracting portion, and compares the calculated core line direction with the line-of-sight direction detected by the line-of-sight direction detecting portion 25e.

In the case where the result of the comparison by the image comparing portion 25d is that the endoscopic image and the VBS image matched within a previously set condition, the aforementioned position and posture calculating portion 25b calculates (acquires) information regarding the position and posture of the distal end of the insertion portion 11 (in other words, information regarding the position of the distal end of the insertion portion 11 and the line-of-sight direction of the objective lens 15).

The aforementioned line-of-sight direction detecting portion 25e is practically equivalent to distal end direction detecting means for detecting the longitudinal direction of the distal end of the insertion portion 11, and the aforementioned position and posture calculating portion 25b calculates (detects) a line-of-sight direction based on information regarding the posture at the time when the information regarding the position and posture of the distal end of the insertion portion 11 was calculated. Therefore, the position and posture calculating portion 25b may also be configured to include the function of the line-of-sight direction detecting portion 25e.

In addition, the image processing portion 25 has a function of an image generating portion that is configured to generate an image to be displayed on the monitor 32 under the control of a display control portion 26a or the like that is provided in the control portion 26 and is configured to control the display of images and the like.

The image processing portion 25 further includes: an image memory 25h that temporarily stores image data such as data of an endoscopic image and a VBS image in a case where the image comparing portion 25d performs an image comparison and also temporarily stores data such as data regarding a position, a posture, and a line-of-sight direction; and a direction change detecting portion (direction change detecting circuit) 25i (indicated by a dashed line in FIG. 1) configured to constitute direction change detecting means for detecting a rotational change in direction of the insertion portion 11 based on a detection result with respect to the presence or absence of a rotational change in the endoscopic image by monitoring the presence or absence of rotational changes in the endoscopic image in a manner that is described later.

Under the control of the display control portion 26a, normally the image processing portion 25 outputs an image signal (video signal) of the bronchial tube shape image 2a generated by the bronchial tube shape image generating portion 23a to the monitor 32, and, as shown in FIG. 2A, the bronchial tube shape image 2a is displayed on the monitor 32 as, for example, a two-dimensional tomogram that was taken at a cross-section along a direction passing through the center of the lumen. Note that the bronchial tube shape image 2a is not limited to a case of being displayed as a two-dimensional tomogram, and may also be displayed as a three-dimensional image. In the case of displaying the bronchial tube shape image 2a as a three-dimensional image, for example, the bronchial tube shape image 2a may be displayed as a projection drawing obtained by a parallel projection method, or as a perspective drawing with which the inside of the lumen can be viewed.

Furthermore, as shown in FIG. 2A, a configuration is adopted so that the core line 35 passing through the center of the lumen of the bronchial tubes 2 is displayed on the bronchial tube shape image 2a displayed on the monitor 32. Although, for example, the bronchial tube shape image generating portion 23a generates the core line 35, the core line 35 may also be generated in the image processing portion 25.

In a case where a user such as a surgeon inserts the insertion portion 11 from the distal end thereof into the bronchial tubes 2, because the core line 35 is displayed, performance of the operation to insert the insertion portion 11 is facilitated by referring to the display. Further, by performing an operation to insert the insertion portion 11 along the core line 35, processing for calculating (estimating) the position and posture of the distal end of the insertion portion 11 by image matching can be performed in a short time.

During an operation to insert the insertion portion 11 to the side of the deep part (end side) of the bronchial tubes 2, in addition to processing to calculate the position and posture in which the distal end of the insertion portion 11 moves under the CT coordinate system, by utilizing matching (image matching) between the endoscopic image and the VBS image the image processing portion 25 can also perform processing to calculate the movement distance.

That is, in a case where both of the images are matching at a certain position, the endoscopic image changes in accordance with an operation to move the distal end of the insertion portion 11 along the core line 35 (for insertion).

In this case, the alignment processing portion 25a or the position and posture calculating portion 25b selects, by image processing, a VBS image that best matches the endoscopic image using VBS images (outputted from the VBS image generating portion 24) in the case where the distal end of the insertion portion 11 moved on a route along the core line 35, and calculates (estimates) a three-dimensional position corresponding to the selected VBS image as the position of the distal end of the insertion portion 11. Accordingly, the position and posture calculating portion 25b or the position calculating portion 25c can also calculate (estimate) a movement distance which the distal end of the insertion portion 11 moved based on the amount of a difference value between two positions.

Note that, since the distal end of the insertion portion 11 is sometimes moved to a position that deviates from the core line 35, a configuration is adopted so that the VBS image generating portion 24 generates a VBS image at a position eccentric from the core line 35 by an appropriate distance, and can output the generated VBS image to the alignment processing portion 25a. Thus, the configuration is such that the range for calculating a position by image matching can be enlarged. The control portion 26 may also be configured to correct route data generated (prior to insertion of the insertion portion 11 of the endoscope 3) by the route data generating portion 29a based on the position of the distal end of the insertion portion 11 calculated by the alignment processing portion 25a.

Further, the control portion 26 includes a function of a condition determining portion (condition determining circuit) 26b that makes a determination as to whether or not the distal end of the insertion portion 11 calculated by the (position and posture calculating portion 25b of the) image processing portion 25 satisfies a predetermined condition. In a case where the result determined by the condition determining portion 26b is that the predetermined condition is satisfied, the relevant information of the position and posture (which corresponds to the line-of-sight direction of the objective lens 15) of the distal end of the insertion portion 11, that is, the position and posture information is recorded in the position and posture information recording portion 27 that is constituted by a memory or the like.

Consequently, the condition determining portion 26b includes a function of a recording control portion (recording control circuit) as recording control means for recording position and posture information in the position and posture information recording portion 27. Note that, in the case of recording position and posture information in the position and posture information recording portion 27, a configuration may be adopted so that, in addition to the position and posture information, a VBS image corresponding to the relevant position and posture information as well as the time of the recording are associated with the position and posture information and recorded in the position and posture information recording portion 27.

By adopting the above described configuration, in the case of presenting information (also referred to as "candidate information") that is presented in order to perform realignment, a VBS image corresponding to the position and posture information can be acquired and displayed in a short time. Further, by recording the time at which the recording is performed, for example, it is possible to perform control so as to selectively display past information that is near to the time at which realignment is performed, or to display a plurality of items of information within a predetermined time interval. Further, displaying the time when displaying (presenting) information makes it easy for the surgeon to ascertain temporal changes in the information.

Note that, even in a case where a VBS image is not recorded, it is possible to acquire and display a VBS image corresponding to the relevant position and posture information based on recorded position and posture information. However, during the process of inserting the insertion portion 11 as far as a target position with respect to which the deep part side of the bronchial tubes 2 is the target, in a case such as when realignment or the like is performed and the coordinate system at the time of a previous alignment is corrected, it is necessary to acquire and display a VBS image in a manner taking the relevant correction or the like into consideration. By also recording the VBS image as described above, a VBS image corresponding to respective items of position and posture information can be displayed in a short time regardless of whether or not realignment is performed.

In the present embodiment, a case where an angle θ formed by a core line direction of the bronchial tubes 2 and a line-of-sight direction detected by the line-of-sight direction detecting portion 25e that was compared by the direction comparing portion 25f is equal to or less than a predetermined threshold value is set as a case that satisfies the aforementioned predetermined condition. Note that, although information regarding the predetermined threshold value is, for example, recorded in the position and posture information recording portion 27 constituted by a memory or the like, a configuration may also be adopted in which the information regarding the predetermined threshold value is recorded in a recording apparatus such as a memory that is other than the position and posture information recording portion 27.

In the aforementioned case where it is determined that the angle θ formed by the core line direction of the bronchial tubes 2 and the line-of-sight direction is equal to or less than the predetermined threshold value, the direction comparing portion 25f controls so as to record the information regarding the position and posture of the distal end of the insertion portion 11 in the position and posture information recording portion 27. Note that, although a configuration in which the condition determining portion 26b is provided inside the control portion 26 is illustrated in FIG. 1, a configuration may also be adopted in which the condition determining portion 26b is provided inside the image processing portion 25.

Furthermore, the direction comparing portion 25f may be configured to include the function of the condition determining portion 26b. Note that, instead of setting the aforementioned predetermined condition using the angle θ formed by the aforementioned two directions, the following inner products may be utilized. That is, a case where respective unit vectors are calculated (set) for the core line direction and the line-of-sight direction, the inner products of the two vectors are calculated, and values of the calculated inner products are equal to or greater than a threshold value may also be set as a case that satisfies the aforementioned predetermined condition.

Since a condition whereby the angle θ formed by the two directions is equal to or less than a predetermined threshold value is a case where the line-of-sight direction of the distal end of the insertion portion 11 is roughly the same as the core line direction, in such a case a state is entered in which a peripheral side of the bronchial tubes 2 can be seen, and if a branching portion is present nearby in that state, the branching portion that is a feature region when inserting the insertion portion 11 is captured in the field of view, thereby facilitating performance of alignment. In contrast, if position and posture information is recorded regardless of whether or not a predetermined condition is satisfied, information that is inappropriate for alignment will be included and it will be difficult to smoothly perform realignment.

In the case of recording position and posture information in the position and posture information recording portion 27, a configuration may be adopted so as to record the position and posture of the distal end of the insertion portion 11 and also a VBS image (together with information of the line-of-sight direction or posture) that corresponds to the relevant position and posture of the distal end, and to record the aforementioned information as candidate information to be presented when presentation is necessary.

That is, the position and posture information recording portion 27 may also be configured to include a position and posture information & VBS image generation information recording portion 27a that records position and posture information of the distal end of the insertion portion 11 as well as a VBS image corresponding to the relevant position and posture information and also VBS image generation information such as information regarding a position in a CT coordinate system used to generate the VBS image and a line-of-sight direction.

Further, since the information recorded in the position and posture information recording portion 27 or the like is information that can be read out and presented (displayed) as candidate information to serve as a candidate for alignment on the monitor 32, it can also be said that the information recording portion 27 includes a function of a candidate information recording portion that records information as candidate information.

Note that a configuration may also be adopted so as to record the aforementioned position and posture information together with a VBS image corresponding to the relevant position and posture information as well as the time of the recording and also an endoscopic image corresponding to the relevant position and posture information in the position and posture information recording portion 27. Further, a configuration may be adopted so that the endoscopic image recorded together with the VBS image that was recorded in the position and posture information recording portion 27 can be utilized in the case of performing realignment.

In the present embodiment, during the course of an operation to insert the insertion portion 11 as far as a target position inside the bronchial tubes 2, in a case where the above described condition that the angle θ formed by the line-of-sight direction and the core line direction is equal to or less than a predetermined threshold value is satisfied, the information regarding the position and posture of the distal end of the insertion portion 11 and the like is recorded in the position and posture information recording portion 27.

Further, a configuration may also be adopted so as to record a point on the core line that is calculated by the core line direction calculating portion 25g and the core line direction instead of the position and posture information of the distal end of the insertion portion 11. In this case, a VBS image is acquired based on the recorded position and posture information and displayed.

Thus, the configuration is such that if the accuracy of position estimation (which utilized image matching) which was performed with respect to the position of the distal end of the insertion portion 11 decreases as the result of an operation that moved the insertion portion 11 after initial alignment was performed by image matching, and it is therefore necessary to perform realignment (or alignment again), information for performing alignment again can be presented as candidate information.

A configuration may also be adopted in which a surgeon can input an instruction to perform alignment again to the image processing portion 25 or the control portion 26 from a keyboard or mouse or the like constituting the input apparatus 31.

When an instruction or the like to perform alignment again is received (or a trigger is inputted), the display control portion 26a of the control portion 26 performs control to read out candidate information for the vicinity of the current position of the distal end of the insertion portion 11 from the position and posture information recording portion 27, and to present the candidate information on the monitor 32 via the image processing portion 25.

The display control portion 26a that performs control for presenting candidate information on the monitor 32 includes a function of a candidate information presentation control portion configured to perform control with respect to candidate information presentation. Further, the image processing portion 25 includes a function of a candidate information generating portion that is configured to display candidate information on the monitor 32 when subjected to the control with respect to candidate information presentation by the display control portion 26a.

Note that the display control portion 26a may also control so as to read out information from the position and posture information recording portion 27 and present the candidate information on the monitor 32 without the information passing through the image processing portion 25. When presenting candidate information on the monitor 32, for example, information regarding the position and posture of the distal end of the insertion portion 11 in the candidate information relating to image comparison (or obtained by image comparison) and a VBS image that corresponds to the relevant candidate information are displayed on the bronchial tube shape image 2a shown in FIG. 2D as a two-dimensional tomogram.

As described above, in a case where the distal end of the insertion portion 11 was moved, the alignment processing portion 25a of the image processing portion 25 estimates (calculates) the distal end of the insertion portion 11 and the posture thereof utilizing image matching. However, in some cases image matching cannot be performed within a set accuracy and an image matching error occurs.

In such a case, the alignment processing portion 25a of the image processing portion 25 generates an image matching error signal, and displays the fact that an image matching error has occurred on the monitor 32. Further, the alignment processing portion 25a sends the image matching error signal to the control portion 26, and the display control portion 26a of the control portion 26 performs control for presenting candidate information on the monitor 32. Further, the monitor 32 forms candidate information presenting means (a candidate information presenting portion) configured to present candidate information to the surgeon.

The surgeon performs realignment processing using the candidate information. By performing realignment processing, the surgeon can continue the operation to insert the insertion portion 11 from the vicinity of the position at which the realignment processing is performed.

Further, in a case where the surgeon determines that the accuracy of the image matching has deteriorated, the surgeon may issue an instruction to perform alignment again to cause the above described processing to be performed.

The endoscope system 1 configured as described above includes: the CT image data storage portion 22 configured to form image storage means for storing previously acquired three-dimensional image information with respect to a subject; the bronchial tube extracting portion 23 configured to form luminal organ extracting means for extracting the bronchial tubes 2 as a predetermined luminal organ from the three-dimensional image information; the objective lens 15 as an objective optical system provided at the distal end of the insertion portion 11 of the endoscope 3; the line-of-sight direction detecting portion 25e configured to form line-of-sight direction detecting means for detecting a line-of-sight direction of the objective lens 15; the direction comparing portion 25f configured to form direction comparing means for comparing a core line direction of the predetermined luminal organ that is extracted by the luminal organ extracting means and the line-of-sight direction; and the position and posture information recording portion 27 configured to form position and posture information recording means for recording information regarding a position and a posture of the distal end of the insertion portion 11 of the endoscope 3 in a case where an angle that the core line direction and the line-of-sight direction form is equal to or less than a predetermined threshold value.

Next, typical processing that is performed in the present embodiment will be described with reference to the flowchart in FIG. 3. When the power of the endoscope apparatus 4 and the insertion support apparatus 5 in the endoscope system 1 shown in FIG. 1 is switched on and the respective portions enter an operational state, in the initial step S1 in FIG. 3, the surgeon sets at least one site at which the position of the distal end of the insertion portion 11 of the endoscope 3 is easy to determine on an endoscopic image, such as a position at the entrance to the bronchial tubes 2 of the patient, as a reference position.

Subsequently, the alignment processing portion 25a of the image processing portion 25 outputs (an image signal of) a VBS image of the VBS image generating portion 24 at the reference position to the monitor 32. The surgeon then designates one reference position using the input apparatus 31, and inserts the distal end of the insertion portion 11 to the designated reference position, and also issues an instruction to perform processing for alignment to the alignment processing portion 25a of the image processing portion 25.

After the alignment processing in step S1 is performed, as shown in step S2, (position and posture calculating portion 25b of) the alignment processing portion 25a estimates (calculates) the position and posture of the distal end of the insertion portion 11 by image matching based on the result of the alignment processing. More specifically, the alignment processing portion 25a uses information of the alignment position as an initial value of the image matching to calculate a VBS image that best matches the endoscopic image by image processing.

Figure 2B:
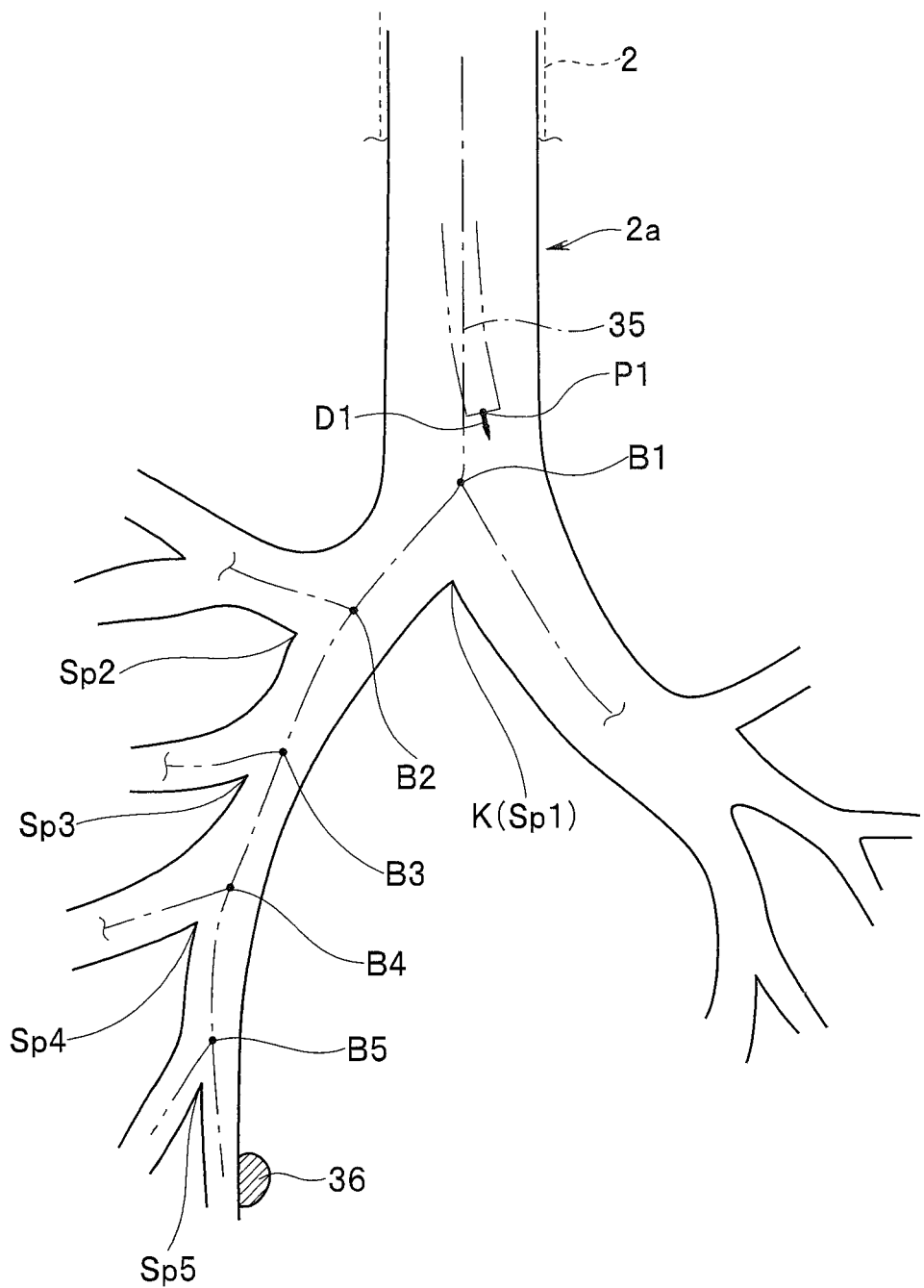
FIG. 2B is a view illustrating a state in which a position and direction of a distal end of an insertion portion of an endoscope are superimposed on the bronchial tube shape image shown in FIG. 2A and displayed.

In step S3, the alignment processing portion 25a determines whether or not the estimation with respect to the position and posture of the distal end of the insertion portion 11 satisfied a predetermined condition (for example, whether the estimated position is inside the bronchial tubes) (that is, whether or not estimation of the position and posture succeeded). If the result determined in step S3 is that the estimation was successful, as shown in step S4, the (image generating portion of the) image processing portion 25 performs image processing to superimpose the position of the distal end of the insertion portion 11 that was estimated by the position and posture calculating portion 25b at the estimated position on the bronchial tube shape image 2a and display the resulting image. FIG. 2B illustrates a display example of an image generated by the image processing in step S4.

FIG. 2B illustrates a state in which the distal end side of the insertion portion 11 of the endoscope 3 that was inserted into the bronchial tubes 2 is indicated by a chain double-dashed line and, in the bronchial tube shape image 2a as a shape image thereof, an estimated position P1 of the distal end of the insertion portion 11 and an estimated longitudinal direction of the distal end or line-of-sight direction D1 corresponding to the posture of the distal end are superimposed (on the bronchial tube shape image 2a) and displayed.

Note that, in FIG. 2B, the longitudinal direction or line-of-sight direction D1 that corresponds to the posture of the distal end of the insertion portion 11 is indicated by an arrow. Further, if the result determined in step S3 is that the estimation was successful, the processing in step S5 is performed along with the processing in step S4.

In step S5, the line-of-sight direction detecting portion 25e calculates the line-of-sight direction D1 of the objective lens 15 based on information regarding the posture of the distal end of the insertion portion 11 that was estimated (calculated) by the position and posture calculating portion 25b. Further, the core line direction calculating portion 25g calculates a core line direction E1 in the vicinity of the position of the distal end of the insertion portion 11 at which the line-of-sight direction D1 was calculated. The direction comparing portion 25f then compares the line-of-sight direction D1 and the core line direction E1, and outputs the comparison result to the condition determining portion 26b.

Next, in step S6, the condition determining portion 26b determines whether or not an angle θ that the line-of-sight direction D1 and the core line direction E1 form is equal to or less than a predetermined threshold value θth that was previously set.

Figure 2C:
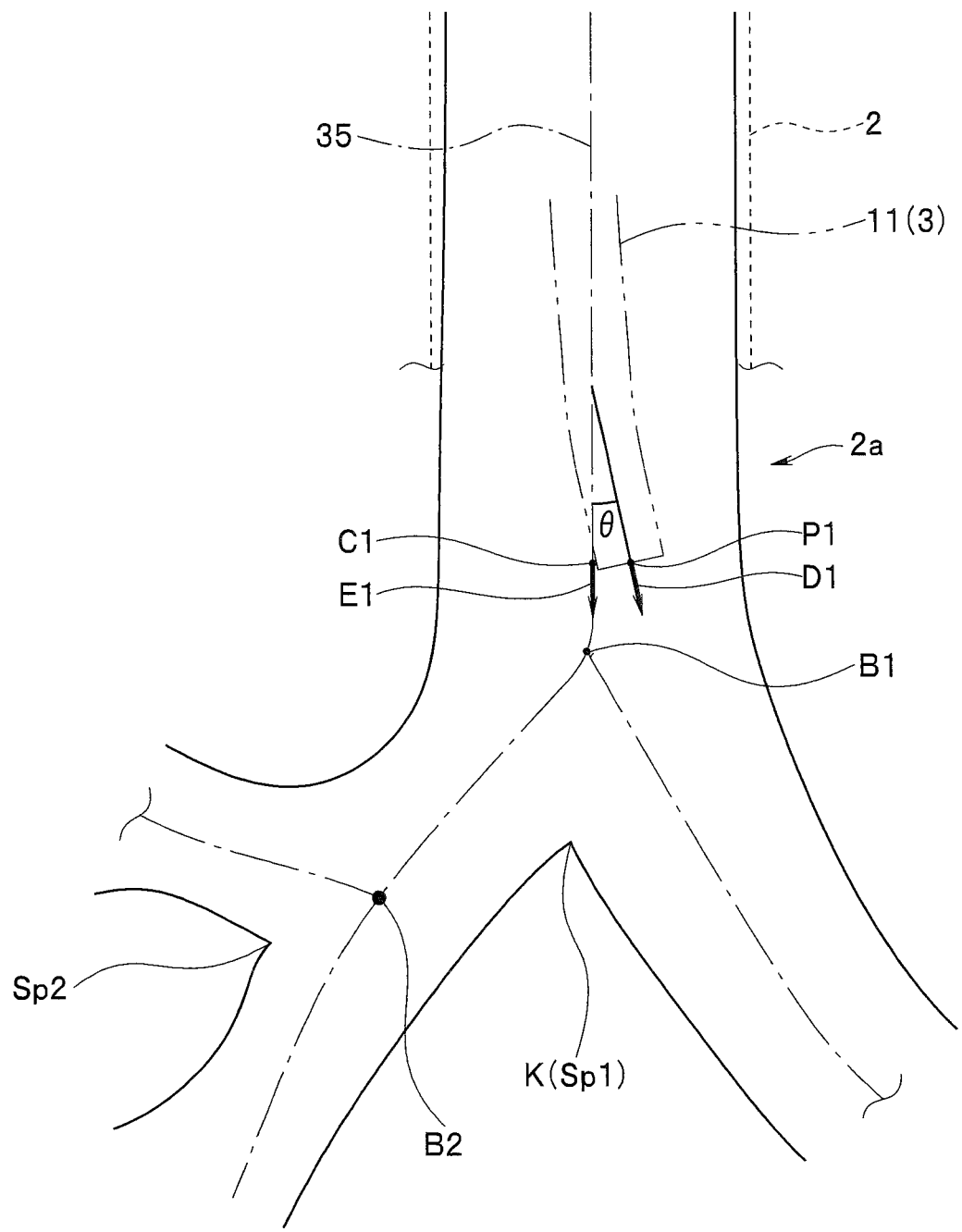
FIG. 2C is an explanatory drawing illustrating the manner of comparing an angle that a line-of-sight direction and a core line direction form.

FIG. 2C illustrates the manner in which the processing in step S5 is performed. In FIG. 2C, the estimated position of the distal end of the insertion portion 11 is denoted by reference character P1, and the line-of-sight direction thereof is denoted by reference character D1. Further, the position of the core line 35 that is closest to the position P1 is denoted by reference character C1. The core line direction calculating portion 25g calculates the core line direction E1 of the core line 35 at the position C1, and the direction comparing portion 25f compares the two directions. Note that, the core line direction calculating portion 25g may also be configured to, for example, calculate the core line direction E1 by taking as the position C1 a position of an intersection point with the core line 35 in the case of a perpendicular line having a length from the position P1 to the intersection point with the core line 35 such that the length is the minimum length. Further, a configuration may also be adopted so as to calculate the core line direction E1 at a position that satisfies a condition of being close to a perpendicular line running from the position P1 to the core line 35.

FIG. 2C illustrates a state in which the angle θ formed by the aforementioned two directions was calculated by the direction comparing portion 25f. The condition determining portion 26b determines whether or not the angle θ calculated as the comparison result is less than or equal to the predetermined threshold value θth. If the determined result is that, as shown in FIG. 2C, the calculated angle θ is less than or equal to the predetermined threshold value θth, next, in step S7, the position and posture information recording portion 27 records the information for the position and posture of the distal end of the insertion portion 11 in the case of the relevant determined result as position and posture information together with a VBS image (that corresponds to the position and posture) and the time that the determined result is obtained. Thereafter, the operation moves to the processing in step S10. Note that, in this case, an endoscopic image corresponding to the relevant position and posture may also be associated with the position and posture and recorded. Further, a configuration may also be adopted so as to record, in step S7, only the position and posture information, or the position and posture information and the time information, or the position and posture information and the VBS image.

In contrast, if the result determined in step S3 is that the estimation failed, the operation moves to the processing in step S8. In step S8, the alignment processing portion 25a generates a signal indicating an image matching error. This signal serves as a signal for presentation of candidate information, and is inputted to the control portion 26

The display control portion 26a of the control portion 26 performs control to present candidate information. The display control portion 26a controls so as to display information including position and posture information recorded in the position and posture information recording portion 27 prior to generation of the signal for presentation of candidate information as well as a VBS image corresponding to the aforementioned position and posture information on the monitor 32 as candidate information. Thereafter, the operation returns to the processing in step S1.

Figure 2D:
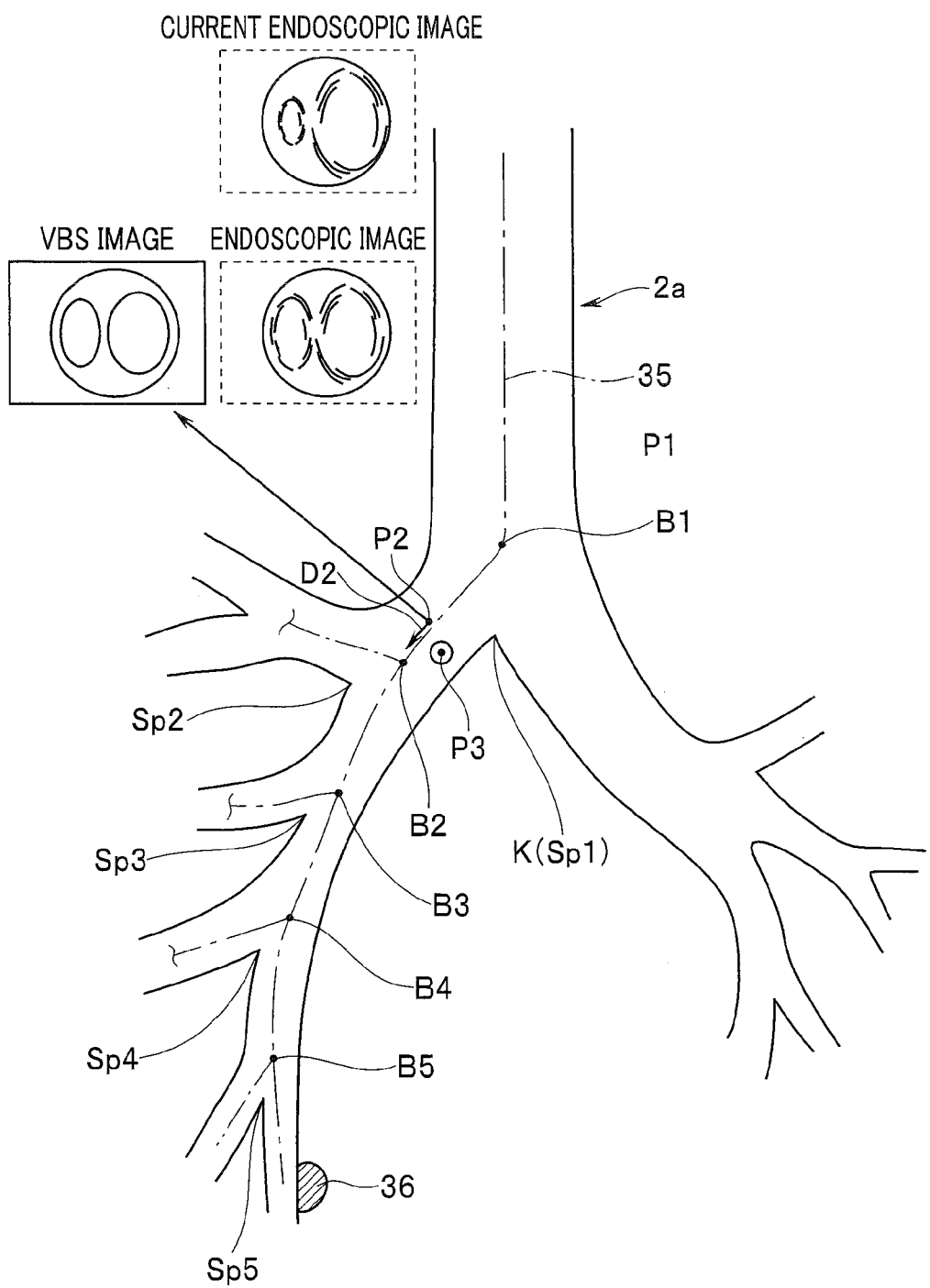
FIG. 2D is a view illustrating a display example of information that is displayed on a monitor when performing a realignment operation.

FIG. 2D illustrates an example of candidate information that is displayed on the monitor 32. In FIG. 2D, a position P3 of the distal end of the insertion portion 11 in the state when the signal indicating an image matching error was generated is schematically illustrated (in practice, the position P3 is undefined). At such time, based on the position and posture information recorded in the position and posture information recording portion 27, a position P2 of the distal end as well as a posture (line-of-sight direction) D2 thereof are displayed on the bronchial tube shape image 2a on the monitor 32, and a VBS image corresponding to the relevant position and posture information is also displayed on the monitor 32.

Further, in the present embodiment, the image processing portion 25 performs image processing so as to display endoscopic images that are indicated, for example, by dashed lines, that correspond to the position and posture information adjacent to the VBS image. In this case, a configuration may also be adopted so to display the endoscopic images at the same display magnification at positions adjacent to the VBS image to facilitate comparison.

In addition, a configuration may be adopted so as to movably display one of the VBS image and the endoscopic image so that the surgeon can use a mouse or the like to superimpose one image on the other image and display the resulting image (synthesized display). Doing so makes it easy for the surgeon to check the degree of image matching.

Furthermore, the image processing portion 25 may perform image processing that displays a current endoscopic image that is inputted from the CCU 8 at the periphery of the VBS image or endoscopic image.

Note that, in FIG. 2D, for example, with respect to a case in which a signal indicating an image matching error was generated, an example is illustrated of candidate information that is based on the most recent position and posture information recorded before the signal was generated. Using the input apparatus 31, the surgeon can also input the number of candidate information items to be displayed, and appropriately set the number of candidate information display items such as VBS images to be displayed at the same time on the monitor 32.

While referring to the VBS image in FIG. 2D, the surgeon, for example, moves the distal end of the insertion portion 11 or the like and performs an alignment operation so that a state is entered in which the current endoscopic image sufficiently matches the VBS image being displayed on the monitor 32. Subsequently, in a set state in which the alignment is such that the images sufficiently match, the alignment processing portion 25a acquires information regarding the viewing point position of the VBS image in the set state and the line-of-sight direction, and uses that information as information regarding the position and posture of the distal end of the insertion portion 11 for the subsequent processing. Thus, the processing of step S2 and thereafter is repeated.

Note that a configuration may also be adopted in which the current endoscopic image shown in FIG. 2D is displayed in a superimposed manner on both a VBS image and an endoscopic image (a reference endoscopic image that was recorded) that matches the relevant VBS image with a predetermined accuracy. In this state, by adjusting the position of the distal end of the insertion portion 11 in a manner that includes the posture thereof, the surgeon can check the degree of alignment between the current endoscopic image and the VBS image, and can also check the degree of alignment between the current endoscopic image and the reference endoscopic image.

While a VBS image is an image that does not take into account minute irregularities such as folds in an inner wall of the bronchial tubes 2, the reference endoscopic image is an image in which the inside of the bronchial tubes 2 was actually picked up at an earlier time. Hence, in some cases it is easier to check the degree of alignment by comparing endoscopic images with each other rather than comparing an endoscopic image and a VBS image. Among the two superimposed images (that is, the superimposed image of the VBS image and the current endoscopic image, and the superimposed image of the reference endoscopic image and the current endoscopic image) in the present embodiment, the surgeon can check the degree of alignment by referring to the superimposed image with which checking of the degree of alignment can be more easily performed (or by referring to both of the superimposed images).

Figure 3:
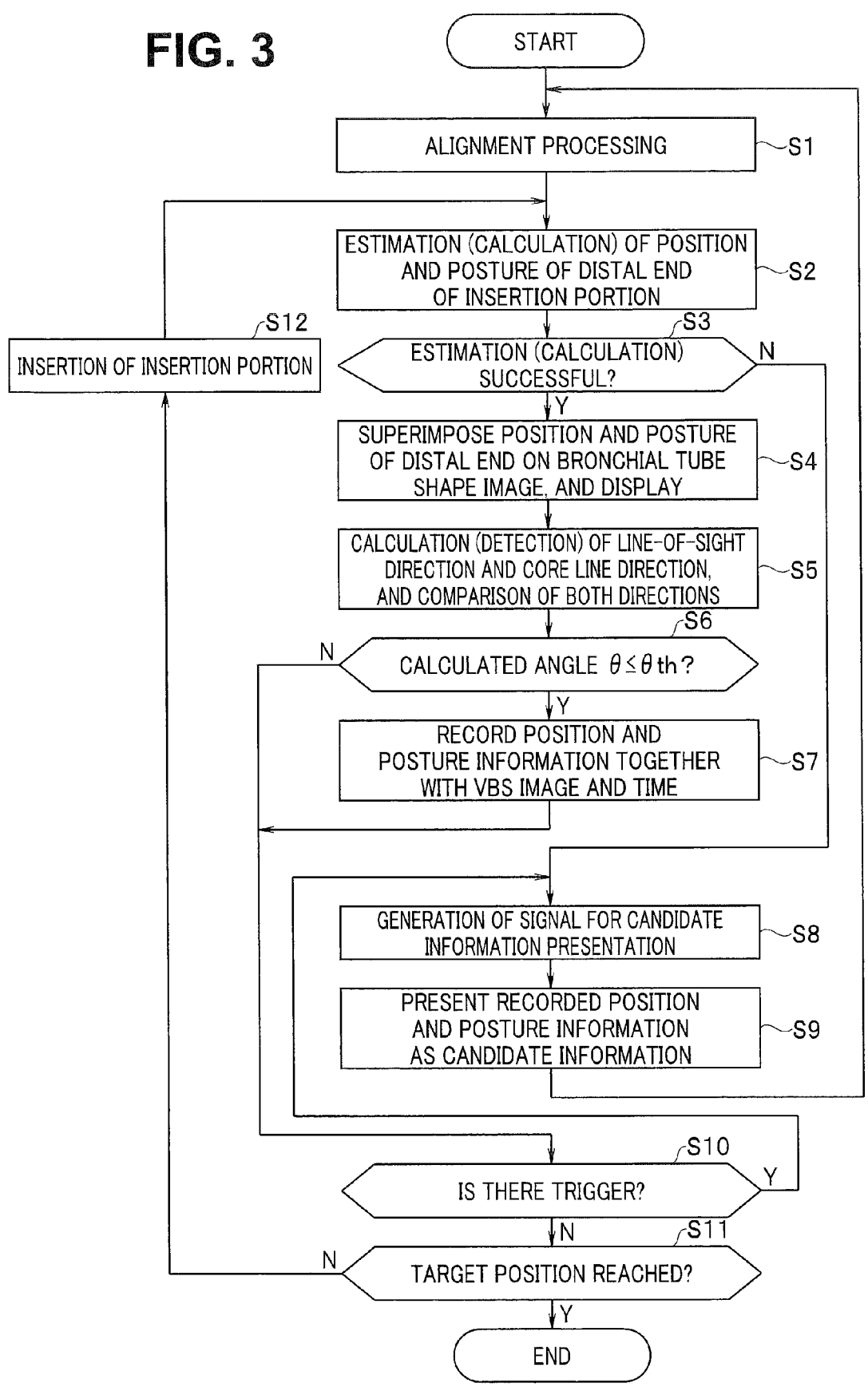
FIG. 3 is a flowchart illustrating an example of typical processing according to the first embodiment.

If the aforementioned angle θ that was calculated in step S6 in FIG. 3 is greater than the predetermined threshold value θth, or if the position and posture information and the like was recorded in step S7, in step S10 the control portion 26 detects whether the surgeon generated a signal (trigger) from the input apparatus 31 to instruct the endoscope system to present candidate information.

This signal (trigger) is an instruction signal the surgeon generates upon deciding to perform alignment again in a case where it cannot be detected that the estimation by image matching failed, for example, a case in which, as a result of the endoscope suddenly moving, although the position estimated by image matching satisfies a predetermined condition (whether the position is inside the bronchial tubes), the actual position is clearly different to the estimated position. If the result determined in step S10 is that there is a trigger, the operation moves to the processing in step S8.

In contrast, if the result determined in step S10 is that there is not a trigger, next, in step S11, the position and posture calculating portion 25b determines whether or not the distal end of the insertion portion 11 has been inserted as far as the target position.

If the distal end of the insertion portion 11 has not been inserted as far as the target position, the surgeon refers to the display of the position and posture information of the distal end of the insertion portion 11 that is displayed on the monitor 32 and, as indicated in step S12, inserts the distal end of the insertion portion 11 to the deep part side of the bronchial tubes 2.

After the processing in step S12 the operation returns to step S2 to perform processing to estimate the position and posture of the distal end of the insertion portion 11. If it is determined in step S11 that the distal end of the insertion portion 11 has been inserted as far as the target position, the insertion operation illustrated in the flowchart in FIG. 3 is ended.

In the present embodiment in which operations are performed as described above, in order to facilitate performance of realignment or the like, the information regarding the posture of the distal end of the endoscope is recorded together with information regarding the position thereof as position and posture information. Therefore, according to the present embodiment, during the operation that the surgeon performs to insert the insertion portion 11, position and posture information of the distal end of the insertion portion 11 is recorded in the position and posture information recording portion 27 as candidate information for presentation that can be used in the case of performing realignment. Therefore, in a case where estimation of the position of the distal end of the insertion portion 11 fails or the like, since candidate information for presentation that is suitable for alignment can be presented, the insertion operation can be smoothly performed.

Further, in the present embodiment, since a configuration is adopted so as to estimate the position and posture of the distal end of the insertion portion 11 that utilizes image processing using image matching, an error is liable to become gradually larger from the state of an initial alignment by means of an algorithm for image processing.

In such a case also, the error can be made sufficiently small by performing realignment by performing image matching again, and it is possible to perform the operation to insert the distal end of the insertion portion 11 to the side of a deeper part from the vicinity of the position with respect to which the realignment was performed.

FIG. 4 illustrates the configuration of an endoscope system 1B according to a first modification of the first embodiment. Relative to the endoscope system 1 in FIG. 1, the endoscope system 1B illustrated in FIG. 4 further includes a position sensor 41 for detecting the position of the image pickup apparatus 16 or the distal end of the insertion portion 11, that is provided at a position in the vicinity of the image pickup apparatus 16 inside the distal end portion 13 of the insertion portion 11.

In addition, at a predetermined position inside the insertion support apparatus 5 that is a position outside the endoscope 3 and the subject, a measurement processing apparatus or measurement processing portion 42 is provided that performs processing for measuring (detecting) a three-dimensional position (also referred to simply as "position") of the position sensor 41. A detection signal generated by the position sensor 41 is inputted to the measurement processing portion 42.

The measurement processing portion 42 includes a function of a position calculating portion (or a position estimating portion) 42b as position calculating means for calculating or estimating the three-dimensional position of the distal end of the insertion portion 11 that is inserted into the bronchial tubes 2 as a predetermined luminal organ using the position sensor 41. In this case, the image processing portion 25 does not include the position calculating portion 25c.

For example, means or a method that utilizes magnetism can be utilized as means or a method for calculating a position (position estimation) in the present modification. An alternating magnetic field emanating from a plurality of antennas 42a connected to the measurement processing portion 42 is sensed by the position sensor 41 that is constituted by a coil, and an amplitude and a phase of a signal detected by the position sensor 41 are detected by the measurement processing portion 42 (which includes an amplitude detecting circuit and a phase detecting circuit) to thereby enable measurement of a distance from the antennas 42a to the position sensor 41. Providing the plurality of antennas 42a that include three or more antennas at known positions that are different to each other makes it possible for the measurement processing portion 42 to specify a three-dimensional position of the position sensor 41.

Note that, a configuration may also be adopted in which an alternating current signal is applied to the coil constituting the position sensor 41 to generate an alternating magnetic field in the periphery thereof, and the alternating magnetic field is then sensed on the antenna 42a side so that the position of the position sensor 41 can be calculated or detected. Although a magnetic position detecting apparatus using a coil has been described as one example, the configuration of the position sensor 41 and the measurement processing portion 42 is not limited to the case described above.

For example, a configuration may be adopted in which a plurality of coils for position detection are disposed at predetermined intervals along the longitudinal direction of the insertion portion 11, and the shape of the insertion portion 11 is estimated based on the positions of the plurality of coils to thereby enable detection of the position of the distal end portion 13 and the like. Positional information for the distal end of the insertion portion 11 that was calculated (estimated) by the measurement processing portion 42 is outputted to the control portion 26 and the image processing portion 25.

In the case of the present modification, alignment is performed between a position (positional information) in a first coordinate system as a CT coordinate system that manages image data with respect to the three-dimensional shape of the bronchial tubes 2 and a position (positional information) in a second coordinate system as a sensor coordinate system that is based on the antennas of the position sensor 41. For example, the image processing portion 25 may also include the function of an alignment processing portion 25a that performs alignment (registration) for the two coordinate systems as well as control thereof, and the control portion 26 may also include the function of an alignment processing portion 26c as indicated by a dashed line.

Figure 5:
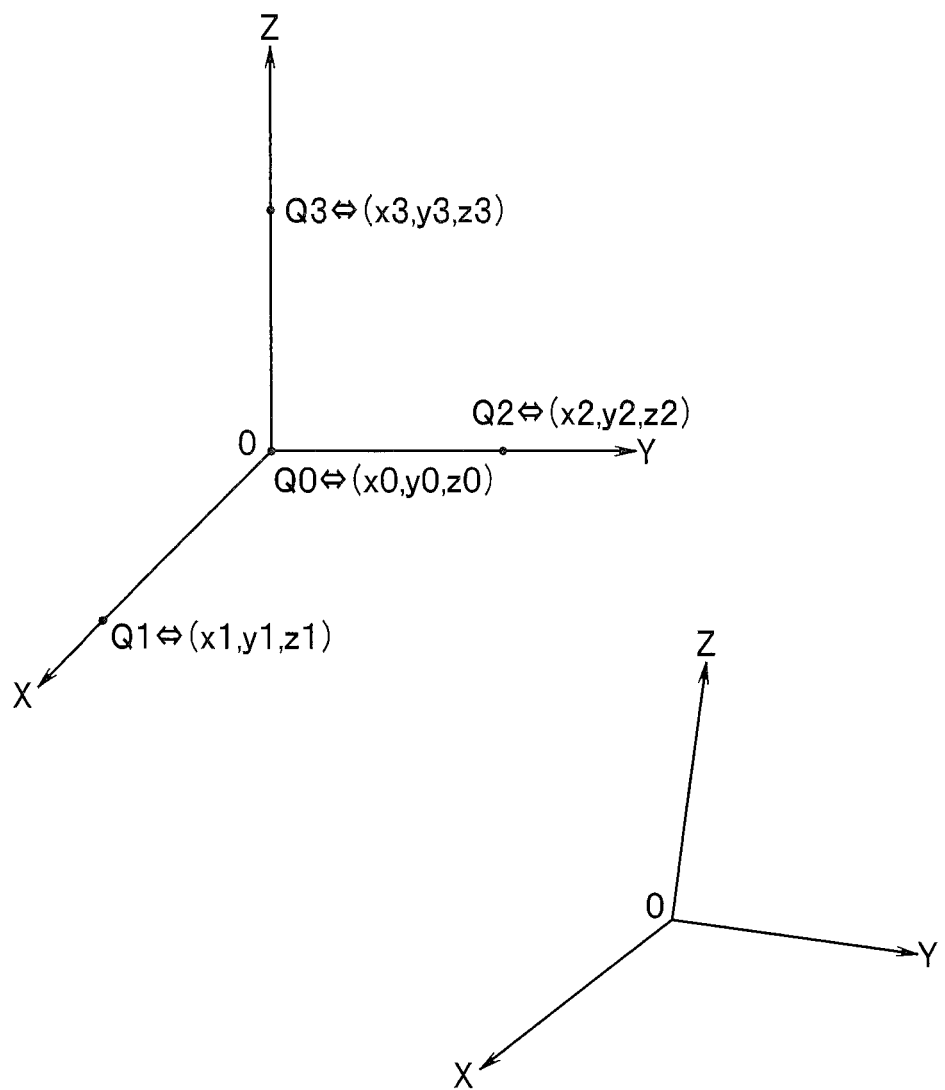
FIG. 5 is an explanatory drawing for describing the alignment of two coordinate systems in the first modification.

FIG. 5 illustrates a drawing for explaining a registration operation. For example, the surgeon sequentially sets the distal end portion 13 (or the position sensor 41) of the endoscope 3 at, for example, four points Q0-Q3 in the vicinity of the entrance to the bronchial tubes 2, and issues an instruction or inputs an instruction from the input apparatus 31 to associate the respective positions in a first coordinate system O-XYZ and a second coordinate system o-xyz with each other. Thus, the input apparatus 31 forms an instruction inputting portion or instruction inputting means for issuing an instruction to associate positions.

For example, the surgeon sequentially sets the distal end portion 13 (or the position sensor 41) to the position Q0 (0, 0, 0) of an origin O, the position Q1 (1, 0, 0) on the X coordinate axis, the position Q2 (0, 1, 0) on the Y coordinate axis, and the position Q3 (0, 0, 1) on the Z coordinate axis in the first coordinate system O-XYZ, and issues instructions to associate the positions. If the positions that the measurement processing portion 42 sequentially measured with respect to the respective positions in the aforementioned instructions are taken as (x0,y0,z0), (x1,y1,z1), (x2,y2,z2) and (x3,y3,z3), the control portion 26 associates the positions, and controls so as to record the position association information in the position and posture information recording portion 27.

The position association information in this case (more specifically, information to the effect that Q0 (0, 0, 0), Q1 (1, 0, 0), Q2 (0, 1, 0) and Q3 (0, 0, 1) in the first coordinate system O-XYZ correspond to (x0, y0, z0), (x1, y1, z1), (x2, y2, z2) and (x3, y3, z3) in the second coordinate system o-xyz, respectively) is recorded in the position and posture information recording portion 27.

Further, the alignment processing portion 26c determines conversion information for associating arbitrary positions in the two coordinate systems using the position association information stored in the position and posture information recording portion 27. The alignment processing portion 26c records the conversion information in the position and posture information recording portion 27.

In FIG. 5, the coordinate positions Q0 (0, 0, 0), Q1 (1, 0, 0), Q2 (0, 1, 0), Q3 (0, 0, 1) and the coordinate positions (x0, y0, z0), (x1, y1, z1), (x2, y2, z2), (x3, y3, z3) that respectively correspond to the aforementioned coordinate positions as shown as Q0⇔(x0, y0, z0), Q1⇔(x1, y1, z1), Q2⇔(x2, y2, z2) and Q3⇔(x3, y3, z3) for simplification. Note that, a configuration may also be adopted that, by omitting one of the four points shown in FIG. 5, performs (determines) the position association using three points instead of the four points shown in FIG. 5.

More specifically, the surgeon causes the distal end portion 13 of the endoscope 3 to sequentially contact the positions designated in the first coordinate system. At this time, a VBS image is used as a method for representing the positions designated in the first coordinate system. That is, the surgeon operates the endoscope 3 so that the VBS image and the endoscopic image appear the same. Further, in a state in which the endoscope 3 is set so that the VBS image and the endoscopic image appear the same, information regarding the line-of-sight direction when the relevant VBS image was generated is acquired (set) as information of the line-of-sight direction (in other words, posture information) of the distal end of the insertion portion 11.

After the processing to associate the positions has been completed in this manner, the surgeon inserts the insertion portion 11 of the endoscope 3 into the bronchial tubes 2 to start to perform an endoscopic examination.

In the present modification, in a case where a positional deviation between the two coordinate systems is clear, such as in a case where a position in the CT coordinate system (first coordinate system) that corresponds to a position of the distal end of the insertion portion 11 that was estimated by the position calculating portion (position estimating portion) 42b does not satisfy a condition of being inside the lumen of the bronchial tubes 2, it is determined that the state is one in which position estimation failed. The remaining configuration is the same as in the first embodiment illustrated in FIG. 1.

With respect to the operations in the present modification, almost the same processing is performed as in FIG. 3 that illustrates the operations performed according to the first embodiment, except for the changes in the present modification that the position of the distal end of the insertion portion 11 is estimated using the position sensor 41, and realignment that is performed in a case where alignment failed is performed by the alignment processing portion 26c of the control portion 26.

In the present modification, the alignment processing portion 25a of the image processing portion 25 includes a function of a second alignment processing portion that is configured to perform alignment by image matching.

Further, the alignment processing portion 25a includes a function of an alignment monitoring processing portion that is configured to monitor the state of alignment of the two coordinate systems by image matching. For example, in a case where the distal end of the insertion portion 11 was inserted into the bronchial tubes 2, the endoscopic image and a position in the second coordinate system calculated by the position calculating portion 42b change accompanying movement of the distal end of the insertion portion 11.

Furthermore, a VBS image that is generated based on positional information of the CT coordinate system (first coordinate system) and is inputted to the image processing portion 25 also changes in accordance with a change in the position in the second coordinate system. The alignment processing portion 25a of the image processing portion 25 monitors the two images, and if the two images deviate to the extent that the amount of deviation therebetween become equal to or greater than a previously set value, the alignment processing portion 25a determines that the state is one in which alignment has failed (or is a state in which alignment is required).

In addition, in the present modification, a case in which there is a clear positional deviation between the two coordinate systems, such as a case where a position in the CT coordinate system (first coordinate system) that corresponds to a position of the distal end of the insertion portion 11 that was estimated by the position calculating portion 42b does not satisfy a condition of being inside the lumen of the bronchial tubes 2, is also determined as being a state in which alignment has failed (a state in which alignment is required). The remaining configuration is the same as in the first embodiment illustrated in FIG. 1.

With respect to the operations in the present modification, almost the same processing is performed as in FIG. 3 that illustrates the operations performed according to the first embodiment, except for the changes in the present modification that the position of the distal end of the insertion portion 11 is estimated using the position sensor 41, and realignment that is performed in a case where alignment failed is performed by the alignment processing portion 26c of the control portion 26.

According to the present modification, a configuration is adopted so that, during an operation in which the surgeon performs to insert the insertion portion 11, position and posture information is recorded in the position and posture information recording portion 27 when a predetermined condition is satisfied, and in a case where estimation of the position of the distal end of the insertion portion 11 fails, the recorded position and posture information can be presented as candidate information for presentation. Hence, according to the present modification, realignment can be performed in a short time, and an insertion operation can be smoothly performed.

Furthermore, in the modification, a configuration is adopted so as to estimate the position of the distal end of the insertion portion 11 using the position sensor 41 after the initial alignment, and a difference from the state of the initial alignment is liable to increase as the distance from the aligned position increases. In such a case also, an error can be made sufficiently small by performing realignment using the position sensor 41 and also using image matching, and it is possible to smoothly perform an operation to insert the distal end of the insertion portion 11 to the side of a deeper part from the vicinity of the position with respect to which realignment was performed.

Figure 6:
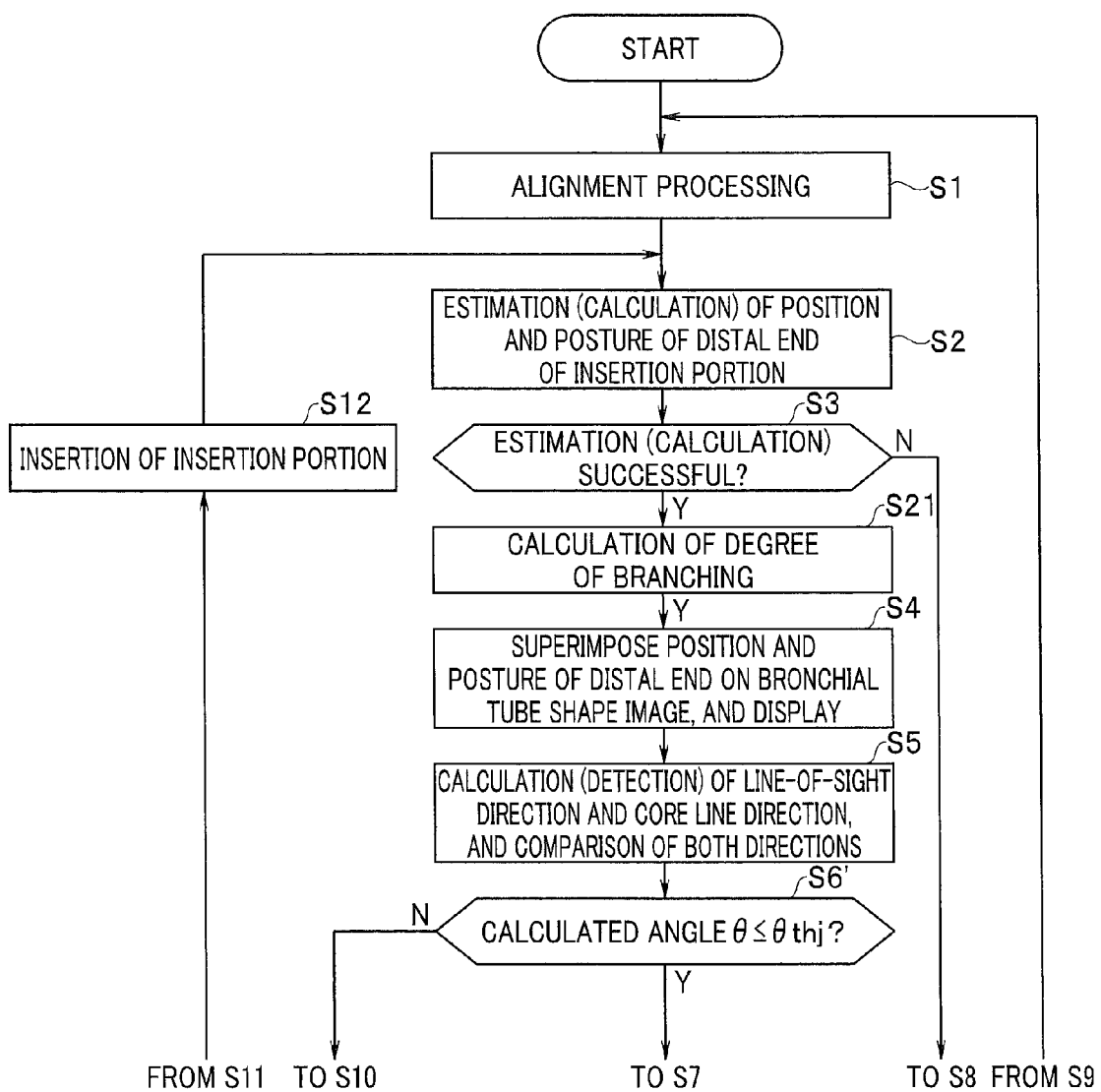
FIG. 6 is a flowchart illustrating one part of processing according to a second modification.

Note that, with respect to the above described first embodiment, a configuration may also be adopted so as to change the threshold value θth in accordance with the degree of branching of the bronchial tubes 2 in the case of determining whether or not the calculated angle θ is less than or equal to the predetermined threshold value θth. One part of processing that is performed in the case of this second modification is illustrated in FIG. 6. In FIG. 6, one part of the processing illustrated in FIG. 3 is changed. Steps S1 to S3 in FIG. 6 are the same as in FIG. 3. In step S21 that is next after step S3, the image processing portion 25 acquires the degree of branching, and thereafter the operation moves to step S4.

The processing in steps S4 and S5 is also the same processing as in FIG. 3. In step S6' which is next after step S5, the condition determining portion 26b determines whether or not the calculated angle θ is less than or equal to a predetermined threshold value θthj that was set in correspondence with the degree of branching. The processing in step S7, which is next after step S6', and from step S7 onwards is the same as in the case illustrated in FIG. 3. Therefore, the steps from step S7 onwards are omitted from FIG. 6.

According to the present modification, it is possible to change a condition for recording the position and posture information in accordance with the position of the distal end of the insertion portion 11 that was inserted into the bronchial tubes 2. For example, in a case where a movement distance from the entrance is large, such as when the distal end of the insertion portion 11 is moved to a peripheral side of the bronchial tubes 2, the accuracy of calculating the position and posture is be liable to decline. That is, there is a possibility that the frequency of recording position and posture information for performing realignment will decrease. Therefore a configuration may also be adopted that, for example, by setting the value of the predetermined threshold value θthj to a progressively larger value as the degree of branching increases, prevents the intervals between positions at which alignment can be performed from becoming large on a peripheral side also. Note that, ordinal numbers of branches at which the bronchial tubes 2 sequentially branch from the insertion opening of the bronchial tubes 2 to the target position on the peripheral side of the bronchial tubes 2 may be used instead of the aforementioned degrees of branching.

Second Embodiment

Next, a second embodiment of the present invention will be described. The configuration in the present embodiment is the same as in FIG. 1 or FIG. 4. According to the present embodiment, with respect to the first embodiment, the current (or present) line-of-sight direction in a case that satisfies the predetermined condition and a line-of-sight direction (recorded line-of-sight direction) Dre with respect to the most recent position and posture information that was recorded in the position and posture information recording portion 27 are compared, and if an angle θd formed by the two line-of-sight directions is greater than or equal to a second predetermined threshold value θdth, the current position and posture information is recorded in the position and posture information recording portion 27.

Note that although in the present embodiment, for example, the condition determining portion 26b determines whether or not the aforementioned angle θd formed by the two line-of-sight directions is greater than or equal to the second predetermined threshold value θdth, a configuration may also be adopted so that the aforementioned determination is perform by a component other than the condition determining portion 26b (for example, the direction comparing portion 25f or the line-of-sight direction detecting portion 25e). Further, information regarding the second predetermined threshold value θdth is recorded, for example, inside the position and posture information recording portion 27.

Figure 7:
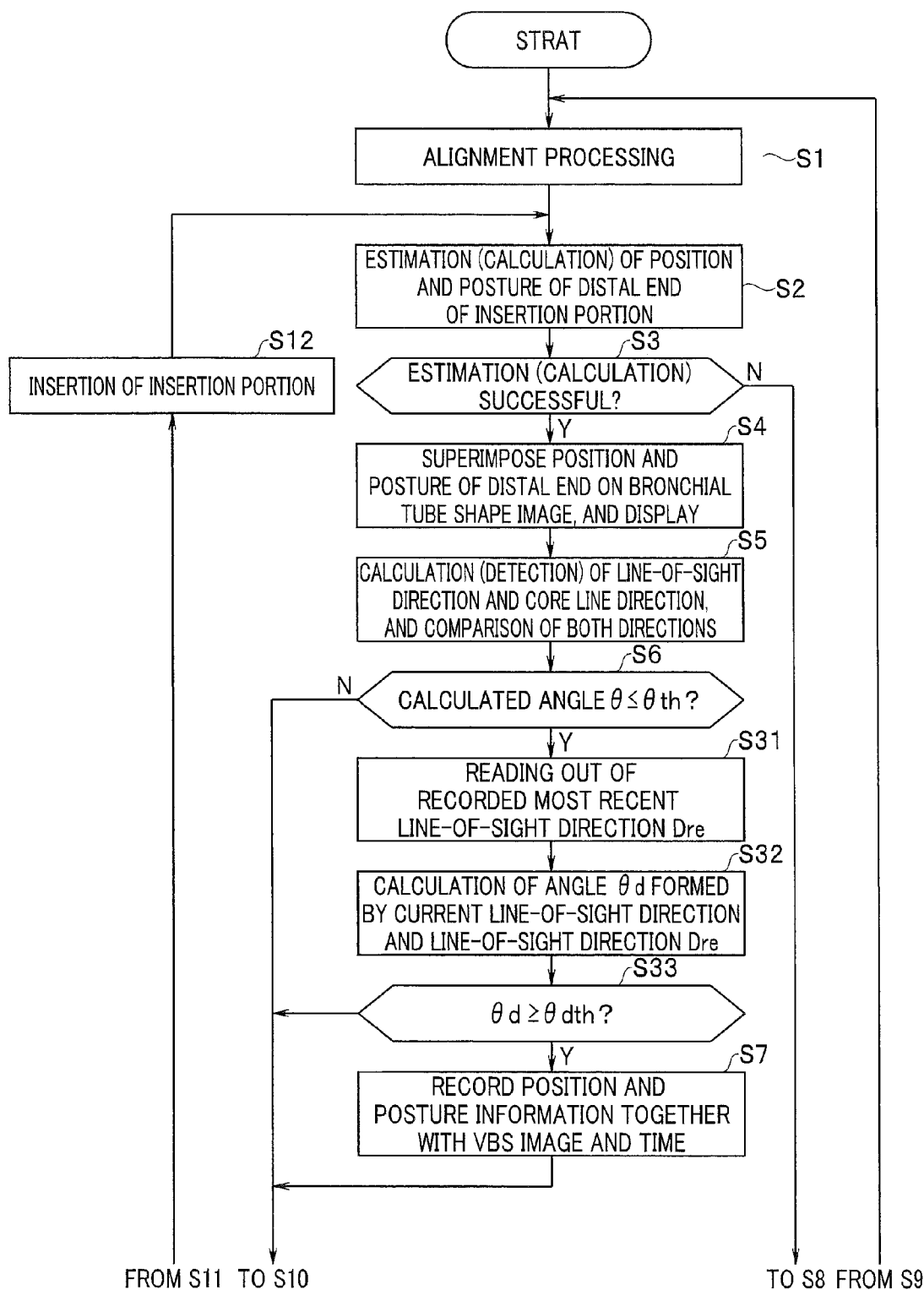
FIG. 7 is a flowchart illustrating one part of processing according to a second embodiment of the present invention.

FIG. 7 illustrates one part of a flowchart showing an example of typical operations in the present embodiment. Only one part of the processing in FIG. 7 differs from the processing in FIG. 3.

Processing that is the same as the processing shown in FIG. 3 is performed from step S1 to step S6 in FIG. 7. In a case where the angle θ calculated in step S6 satisfies the condition of being less than or equal to the predetermined threshold value θth, next, in step S31, for example, the condition determining portion 26b reads out the line-of-sight direction Dre in the most recent position and posture information recorded in the position and posture information recording portion 27, and sends the line-of-sight direction Dre to the image processing portion 25.

In step S32, for example, the direction comparing portion 25f calculates an angle θd formed by the current line-of-sight direction that was calculated in step S5 and the line-of-sight direction Dre that was read out from the position and posture information recording portion 27, and sends the calculated angle θd to the condition determining portion 26b. In step S33, the condition determining portion 26b determines whether or not the angle θd is greater than or equal to the second threshold value θdth.

If the determined result is that the angle θd is greater than or equal to the second predetermined threshold value θdth, next, in step S7, the current position and posture information is recorded together with the relevant VBS image and time in the position and posture information recording portion 27.

On the other hand, if the determined result is that the angle θd is not greater than or equal to the second predetermined threshold value θdth, the operation moves to the processing in step S10. The other processing in FIG. 7 is the same as in the corresponding steps FIG. 3.

In the first embodiment, if it is determined that the angle θ calculated in step S5 is less than or equal to the predetermined threshold value θth in the subsequent step S6, the (current) position and posture information at the time point at which the determination was performed is chronologically recorded in the position and posture information recording portion 27.

In contrast, in the present embodiment, if it is determined that the angle θ is less than or equal to the predetermined threshold value θth in step S6, a line-of-sight direction Dre in the position and posture information that was recorded in the position and posture information recording portion 27 immediately prior to the relevant time point is read out, an angle θd formed by the line-of-sight direction Dre and the line-of-sight direction at the relevant time point is calculated, and the position and posture information at the relevant time point is chronologically recorded in the position and posture information recording portion 27 only in a case where the determined result is that the calculated angle θd is greater than or equal to the second predetermined threshold value θdth.

In other words, in the first embodiment, if an angle θ formed by the line-of-sight direction and the core line direction satisfies a condition of being sufficiently small, position and posture information at the time point at which the condition is satisfied is repeatedly recorded, while in contrast, in the present embodiment, unless an angle θd formed by the line-of-sight direction at the relevant time point and the line-of-sight direction recorded immediately prior thereto is greater than or equal to a second predetermined threshold value θdth, the position and posture information at the relevant time point is not recorded.

Accordingly, in the present embodiment, relative to the first embodiment, the position and posture information for the relevant time point is recorded only in a case where there is a significant change in the line-of-sight direction relative to the line-of-sight direction recorded immediately prior thereto. Further, a configuration is adopted so as to avoid excessively recording position and posture information of similar conditions. In a case where the distal end of the insertion portion 11 passes through a branching position from a position to which the distal end of the insertion portion 11 was inserted and moves to the side of a bronchial branch that is a peripheral side, it can be anticipated that the line-of-sight direction will change when passing through the branching position, and hence a configuration is adopted so that the position and posture information at the time of such a movement can be recorded.

According to the present embodiment, as well as having the operations and/or effects such that position and posture information can be recorded in approximately the same manner as in the first embodiment, excessive recording of similar position and posture information can be avoided, and recording can be narrowed down to position and posture information that is of an appropriate information amount. Therefore, it is possible to present only position posture information that is close to the required minimum amount to a user such as a surgeon, and when performing realignment, the alignment can be smoothly performed without presenting too much candidate information. In other words, the ease-of-use with respect to the user can be improved. Further, in the present embodiment, a configuration may also be adopted so as to automatically determine the aforementioned second predetermined threshold value θdth in the following manner.

For example, the position and posture information recording portion 27 is provided that forms a branch information recording portion that is configured to record branch information that includes a three-dimensional position and a branching angle of one or more branch points at which the bronchial tubes 2 branch during the course of reaching the relevant target position in route data from the insertion starting position of the distal end of the insertion portion 11 to the target position in the vicinity of the target site 36 that is generated by the route data generating portion 29a that is described above. The branch information recording portion may then automatically determine the second predetermined threshold value θdth in accordance with the branch information of the branch points, and the direction comparing portion 25f may use the thus-determined second predetermined threshold value θdth to compare an angle θd formed by a past line-of-sight direction that was recorded in the position and posture information recording portion 27 and the current line-of-sight direction detected by the line-of-sight direction detecting portion 25e with the determined second predetermined threshold value θdth.

The branch information recording portion may also be configured to, on the basis of the three-dimensional position of the distal end of the insertion portion 11 at the time that the current line-of-sight direction was detected by the line-of-sight direction detecting portion 25e, automatically determine a second predetermined threshold value θdth with respect to branch information of a next branch point that is present at a position that is further along the target position side relative to the relevant three-dimensional position.

In other words, (candidate information of) respective second predetermined threshold values θdth are recorded in association with branch information including a three-dimensional position and a branching angle of each branch point at which the bronchial tubes 2 branch during the course of reaching the target position, and based on the information for the three-dimensional position at which the distal end of the insertion portion 11 is currently at, the branch information recording portion selectively determines a second predetermined threshold value θdth that was previously recorded in association with branch information of a branch point that the distal end of the insertion portion 11 is predicted to reach next.

By adopting this configuration, in a case where the distal end of the insertion portion 11 is inserted to the target site 36 side, the second predetermined threshold value θdth can be automatically set even in a case where branching angles of branch points along the relevant route are different, and thus the work of the surgeon to insert the distal end of the insertion portion 11 can be effectively supported.

Note that, in the present embodiment a configuration is adopted in which the most recent line-of-sight direction Dre that was recorded is read out in step S31, and the angle θd formed by the line-of-sight direction Dre and the current line-of-sight direction is then calculated. However, as a modification thereof, a configuration may be adopted in which a line-of-sight direction Dren that was recorded a number of times n (where n is an integer) prior to the current line-of-sight direction, including the case of the most recent line-of-sight direction, is read out (for example, the most recently recorded line-of-sight direction corresponds to n=1 that is the operation one time prior to the current operation), and an angle that the line-of-sight direction Dren forms with the current line-of-sight direction is then calculated.

Subsequently, it is determined whether or not the calculated angle is greater than or equal to a threshold value θdth' corresponding to the aforementioned second threshold value θdth, and if the determined result is that the calculated angle is greater than or equal to the second threshold value θdth', the position and posture information is recorded. Note that, the operations of the present modification are operations in which the line-of-sight direction Dren that was recorded a number of times n prior to the current line-of-sight direction is read out as the processing in step S31 in FIG. 7, and the line-of-sight direction Dren is used instead of the line-of-sight direction Dre in step S32.

The present modification has intermediate operations and/or effects relative to the respective operations and/or effects of the first and second embodiments.

Third Embodiment

Next, a third embodiment of the present invention will be described. The configuration of the present embodiment is the same as the configuration in FIG. 1 or FIG. 4. Relative to the first or second embodiment, the present embodiment further includes means for reducing the frequency of recording position and posture information.

In the first embodiment, at a site at which the bronchial tube diameter (inner diameter of bronchial tubes) is narrow, because the frequency at which the inserted insertion portion 11 is inserted parallel to the core line becomes high, the recording frequency also increases, and there is a possibility that the position and posture information that is recorded will increase beyond an information amount that the surgeon desires.

Further, in the second embodiment and the modification thereof, if the insertion portion 11 wobbles at a site at which the bronchial tube diameter is large while being inserted, the recording frequency will also increase, and there is a possibility that the position and posture information that is recorded will increase beyond an information amount that the surgeon desires.

When the position and posture information that is recorded increases beyond the amount of information that is required, the usability for the surgeon declines.

Therefore, in the present embodiment, prior to the processing to record position and posture information in step S7 in FIG. 3, it is further determined whether or not at least one of the following conditions a) to c) is satisfied. Processing is performed that restricts recording so as to perform recording in a case that satisfies the following conditions, to thereby reduce the frequency at which position and posture information is actually recorded.

a) a distance from the position of the distal end that was recorded the previous time is greater than or equal to a threshold value Lth;

b) a time when an image of a branch is visible in the endoscopic image;

c) a distance between the position of the distal end of the insertion portion 11 and a point on the core line 35 that is closest to the position of the distal end is less than or equal to a threshold value Lth2.

Figure 8:
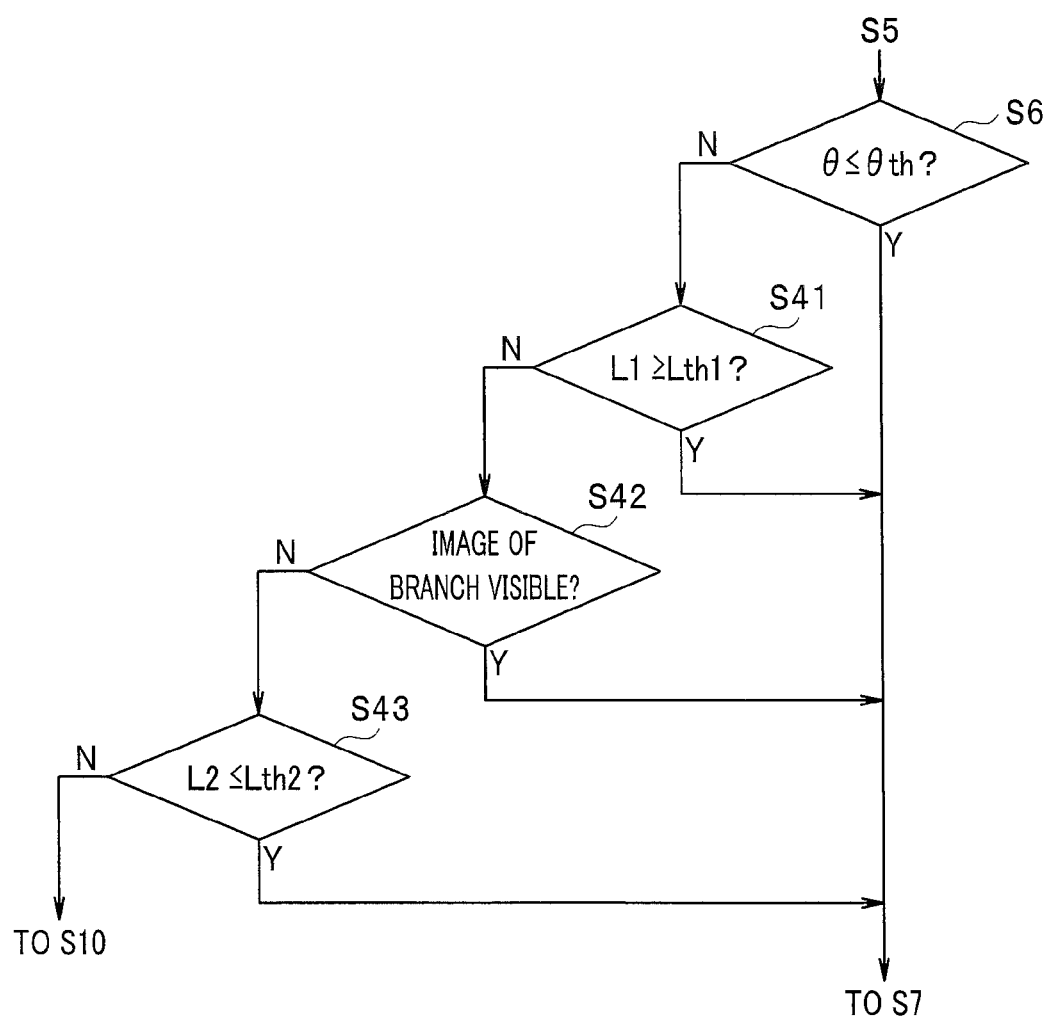
FIG. 8 is a flowchart illustrating one part of processing according to a third embodiment of the present invention.

FIG. 8 illustrates a flowchart showing an example of typical processing according to the present embodiment.

In FIG. 8, the processing from step S1 to step S6 is the same as in the corresponding steps in FIG. 3, the processing in steps S41 to S43 that are described below is provided between step S6 and step S7, and the remaining processing is the same as in FIG. 3.

If the angle θ calculated in step S6 satisfies the condition of being less than or equal to the predetermined threshold value θth, in step S41, for example, the position calculating portion 25c having a function of a distance calculating portion determines whether or not a distance L1 from the position of the distal end that was recorded the previous time is greater than or equal to a threshold value Lth1.

If this condition is satisfied, the operation advances to the processing in step S7, while if this condition is not satisfied, the operation moves to the processing in step S42. In step S42, a branch image recognizing portion that recognizes an image of a branch in an endoscopic image by image processing that is provided in the image processing portion 25 performs a determination as to whether or not the condition that an image of a branch is visible in the endoscopic image is satisfied. More specifically, the endoscopic image is binarized using a certain threshold value, and a determination is performed with respect to whether or not there is a plurality of dark portions that have a certain number of pixels.

If this condition is satisfied, the operation proceeds to the processing in step S7, while if this condition is not satisfied, the operation moves to the processing in step S43. In step S43, for example, the position calculating portion 25c that has a function of a distance calculating portion determines whether or not the condition is satisfied that a distance L2 between the position of the distal end of the insertion portion 11 and a point on the core line 35 that is closest to the relevant position of the distal end is less than or equal to the threshold value Lth2.

If the aforementioned condition is satisfied, the operation proceeds to the processing in step S7, while if the condition is not satisfied the operation moves to the processing in step S10.

Note that, the aforementioned threshold values Lth1 and Lth2 for the distance may be set in the following manner.

The threshold values Lth1 and Lth2 may be set to the same value for all of the bronchial tubes 2, may be set to a value that is in accordance with the value of the bronchial tube diameter for each of the bronchial tubes 2, or may be set to a value in accordance with the site or the degree of the bronchial tubes.

Further, the respective distances L1 and L2 may be a distance along a straight line between two points, or may be calculated (measured) based on the distance on the core line 35 from a point on the core line 35 that is closest to the position of the distal end of the insertion portion 11 to the branch point.

According to the present embodiment, since a configuration is adopted so as to reduce (curtail) excessive recording of position and posture information, the usability for the user can be improved. In addition, the present embodiment has the same effects as in the first embodiment.

Note that the order of the processing with respect to step S6 and steps S41 to S43 in FIG. 8 may be altered. For example, the processing in steps S41 to S43 may be performed before performing the determination processing in step S6, and the determination processing in step S6 may then be performed if any one of the conditions is satisfied.

Further, for example, a configuration may be adopted so as to monitor whether or not the distal end of the insertion portion 11 moved by an amount that is greater than or equal to a predetermined distance interval from the position the distal end of the insertion portion 11 was located at the previous time that the distance calculating portion recorded position and posture information, perform the determination processing in step S6 if the distal end of the insertion portion 11 moved by an amount that is greater than or equal to the predetermined distance interval, and record the position and posture information in step S7 if the determination condition is step S6 is satisfied.

Further, on the premise of performing the processing in step S6 (or the processing in step S5 and S6), a configuration may be adopted such that the distance calculating portion monitors whether or not the distal end of the insertion portion 11 moved by an amount greater than or equal to a predetermined distance interval from the position of the distal end of the insertion portion 11, and if the distal end of the insertion portion 11 moved by an amount greater than or equal to the predetermined distance interval, the processing in step S6 (or the processing in step S5 and S6) is performed.

A configuration may also be adopted so as to record the position and posture information in step S7 if the determination condition in step S6 is satisfied. In this case, the operations include the direction comparing portion 25f as direction comparing means performing a comparison between the line-of-sight direction and the core line direction in a case where the movement distance of the distal end of the insertion portion 11 is greater than or equal to a predetermined distance interval within a lumen of the bronchial tubes 2.

Fourth Embodiment

Next, a fourth embodiment of the present invention will be described. Relative to the first embodiment, the present embodiment further includes a direction change detecting portion 25i that is indicated by a dashed line in FIG. 1 and FIG. 3, and the direction change detecting portion 25i compares the direction (orientation) of an endoscopic image that was picked up through the objective lens 15 that is fixed in an observation window (image pickup window) in the distal end of the insertion portion 11 of the endoscope 3 and the direction of an endoscopic image when position and posture information was recorded the previous time.

In a case where a condition that an angle θro formed by the two directions is greater than or equal to a threshold value θroth is satisfied, in other words, in a case where the angle θro formed by the two directions is sufficiently large, the relevant position and posture information is recorded. Note that, the meaning of term "direction (orientation) of the endoscopic image" is the same as the term "direction around the circumference of the insertion portion 11" that is described below.

The surgeon often performs an operation to turn (twist) the insertion portion 11 when passing (inserting) the distal end of the insertion portion 11 through to the side of bronchial branches that branch on the peripheral side of the bronchial tubes 2 (or bronchial branches) in a state in which the distal end of the insertion portion 11 is currently being inserted. In the present embodiment, recording of position and posture information multiple times in the same bronchial branch is avoided in the manner described below by utilizing the aforementioned operation.

By detecting an operation that is normally performed once when passing (inserting) the distal end of the insertion portion 11 through to the side of branching bronchial branches, and recording the position and posture information at the time the operation is detected, recording of position and posture information multiple times in the same bronchial branch that occurs in a case where such detecting is not performed is avoided.

Note that a VBS image that is used (is compared with an endoscopic image) in image matching is, in a state in which (the objective lens 15 of) the distal end of the insertion portion 11 has been set in a predetermined direction (orientation) together with a viewing point and a line-of-sight direction in a CT coordinate system, generated in correspondence with light that is subjected to photoelectric conversion by a CCD 16 that is similarly fixed in a predetermined direction (orientation). Note that, directions (around the circumference of the insertion portion 11) of the image pickup surface of the CCD 16 are previously set so that the upward and downward directions in a case where an endoscopic image is displayed on the monitor 9 match upward and downward bending directions in the case of bending the bending portion 19.

Consequently, when image matching is performed and information of the actual position and posture of the distal end of the insertion portion 11 is acquired based on information of the CT coordinate system, information regarding the direction (orientation) around the circumference of the insertion portion 11 can also be acquired.

In the present embodiment, when recording position and posture information in the position and posture information recording portion 27, information regarding a direction (orientation) of the endoscopic image (or a direction (orientation) around the circumference of the insertion portion 11) is also recorded. Further, a configuration is adopted so that information regarding a direction (orientation) of the endoscopic image can be referred to (in order to calculate a change in direction) based on the information recorded in the position and posture information recording portion 27.

The direction (orientation) of the endoscopic image does not change unless the insertion portion 11 is rotated in a circumferential direction thereof. Therefore, the direction change detecting portion 25$i$ has a function of direction change detecting means for detecting a change in the direction of an endoscopic image, or a change in a direction around the circumference of the insertion portion 11.

Figure 9:
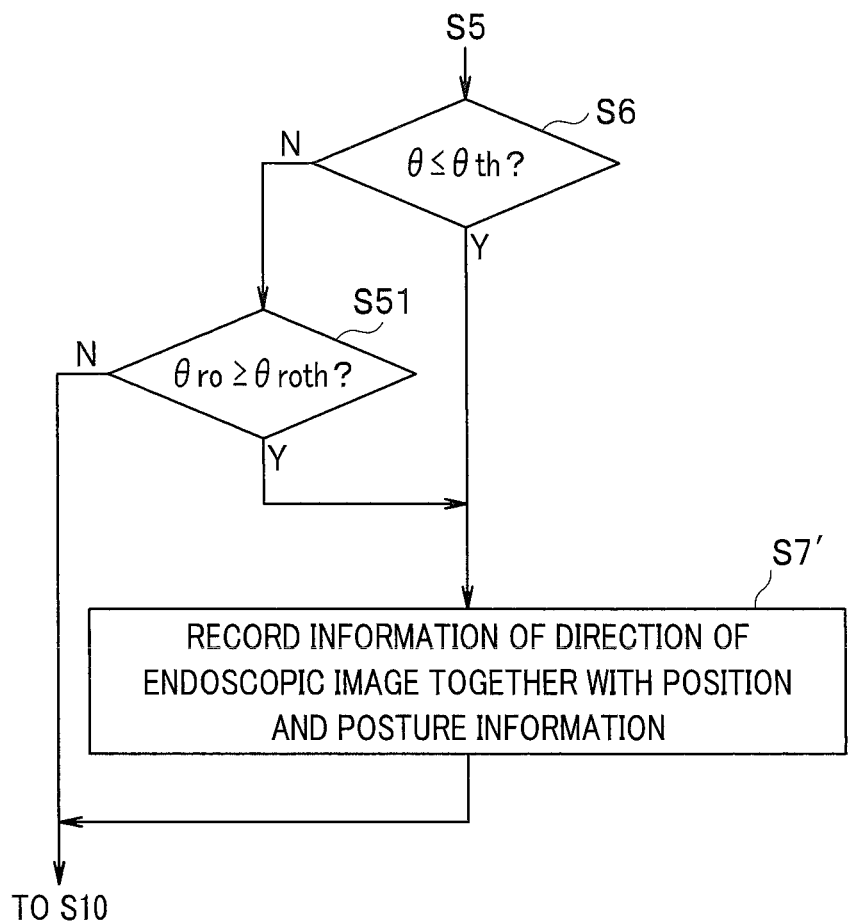
FIG. 9 is a flowchart illustrating one part of processing according to a fourth embodiment of the present invention.

Note that, the direction change detecting portion 25$i$ may be configured to detect a change from a predetermined direction (or a reference direction) of an endoscopic image or the like in the case of detecting a change in the direction of the endoscopic image or a change in the direction around the circumference of the insertion portion 11. For example, a configuration may be adopted in which the upward direction of the endoscopic image is set as the predetermined direction, and a change from the upward direction of the endoscopic image is detected. FIG. 9 illustrates one part of typical processing in the present embodiment.

In FIG. 9, the processing from step S1 to step S6 is the same processing as in FIG. 3. Further, in step S6, when the condition that the calculated angle $\theta$ is not less than and not equal to the predetermined threshold value $\theta$th is satisfied, the operation advances to the processing in step S51.

In step S51, the direction change detecting portion 25$i$ calculates an angle $\theta$ro formed by the direction of the endoscopic image in the current state of the distal end of the insertion portion 11 and the direction of an endoscopic image at the time of the previous recording (the recording performed immediately prior to the current time), and also determines whether or not the angle $\theta$ro formed by the two directions satisfies the condition of being greater than or equal to the threshold value $\theta$roth.

If the result determined in step S51 is that the condition is satisfied, in step S7', as described above, the current position and posture information as well as information regarding the direction (orientation) of the endoscopic image are record in the position and posture information recording portion 27. If the result determined in step S51 is that the condition is not satisfied, the operation moves to the processing in step S10. The other processing is the same as the case illustrated in FIG. 3.

According to the present embodiment, position and posture information of an appropriate amount can be recorded without excessively recording the position and posture information, and thus the usability (convenience) for the user can be improved. In addition, the present embodiment has the same effects as in the first embodiment.

In the above described fourth embodiment, in step S51 the angle $\theta$ro formed by the current direction (around the circumference) of the distal end of the insertion portion 11 and the direction that was recorded the previous time were compared. However, a configuration may also be adopted in which an angle $\theta$ron formed by the current direction (around the circumference) of the distal end of the insertion portion 11 and the direction that was recorded n times before the current operation are compared, and if the angle $\theta$ron is greater than or equal to a threshold value $\theta$ronth, the current position and posture information is recorded in the position and posture information recording portion 27. Note that, in a case where information regarding the direction of the endoscopic image is acquired, a configuration may also be adopted in which a difference angle from a predetermined direction (or a reference direction) is calculated, and a difference angle from the upward direction is also recorded in the case of recording position and posture information in the position and posture information recording portion 27.

Fifth Embodiment

Next, a fifth embodiment of the present invention will be described. The present embodiment is a combination of the above described embodiments (including the modifications), and the configuration thereof is the same as in FIG. 1 or FIG. 4. In the present embodiment, any two or more of the conditions of the above described embodiments are used in a manner in which the conditions are switched for each region in which the distal end of the insertion portion 11 is present.

Figure 10:
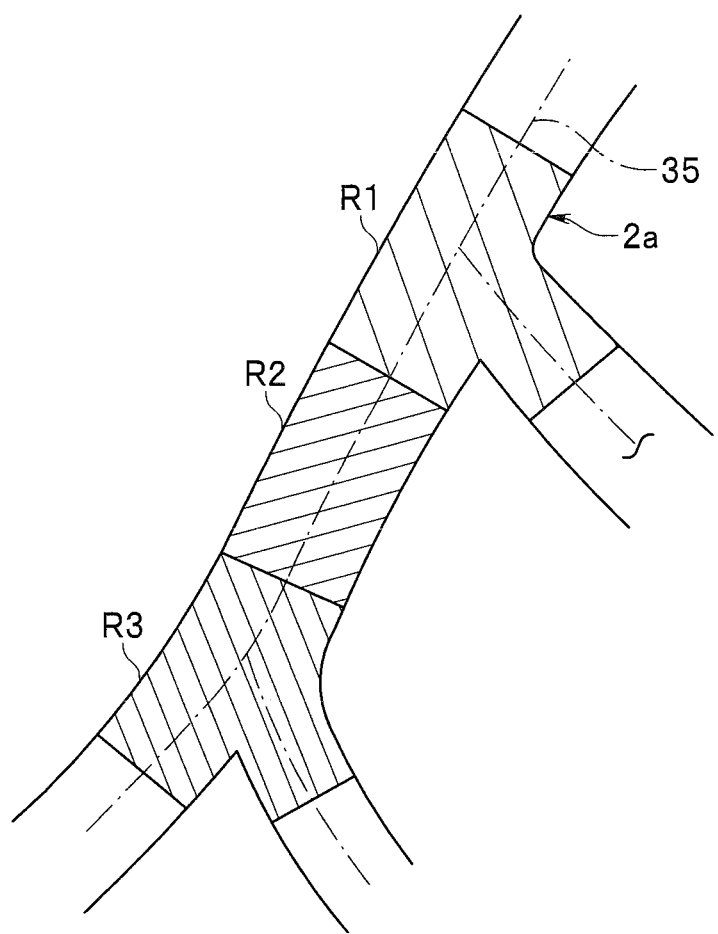
FIG. 10 is an explanatory drawing for describing operations according to a fifth embodiment of the present invention.

FIG. 10 is an explanatory drawing of operations in the present embodiment. In the present embodiment, in a case where the insertion portion 11 has been inserted into the bronchial tubes, in a region R1 in which the distal end of the insertion portion 11 is present, a condition of the first embodiment, a condition of second embodiment is applied in a region R2, and a condition of the third embodiment is applied in a region R3.

Methods for setting the regions Rk (k=1, 2, 3, . . . ) are described hereunder.

The respective regions are set as follows:

a) a region up to a position that is a certain distance on the core line from a branch point is set, and the other regions are set as shown in FIG. 10;

b) a region included in a sphere centered on a branch point is set, and the other regions are set;

c) regions are set based on a distance from the carina;

d) regions are set based on degrees of the bronchial tubes;

e) regions are set based on bronchial tube diameters calculated based on tomographic images; and f) regions are set based on a distance from the position of the previous restart (realignment).

Further, a plurality of these conditions may be combined.

According to the present embodiment, as well as having the effects of the above described embodiments, a user can moreover select in greater detail the conditions under which to record the relevant information.

In addition, an embodiment obtained by partially combining a plurality of the above described first to fourth embodiments, including the foregoing modifications, also belongs to the present invention.

Further, when generating a bronchial tube shape image or a VBS image, instead of extracting three-dimensional image data of the bronchial tubes 2 as a predetermined luminal organ from CT image data, the relevant image may be generated directly by volume rendering based on CT image data.

What is claimed is:

1. An endoscope system capable of previously acquiring shape information that is associated with positional information regarding a luminal organ of a subject, comprising:

a position and posture calculating portion that estimates a position of a distal end of an endoscope insertion portion and a longitudinal direction of a distal end portion of the endoscope insertion portion;

a condition determining portion that, based on the shape information at a position of the distal end of the endoscope insertion portion estimated by the position and posture calculating portion, determines whether or not an angle that a core line direction of a core line that is positioned at approximately a center of the luminal organ and a longitudinal direction of the distal end portion of the endoscope insertion portion that is estimated by the position and posture calculating portion is equal to or less than a predetermined threshold value; and a position and posture information recording portion configured to, in a case where an angle that the core line direction and the longitudinal direction of the distal end portion of the endoscope insertion portion form is equal to or less than a predetermined threshold value, record information regarding the position of the distal end of the endoscope insertion portion and the longitudinal direction of the distal end portion of the endoscope insertion portion that is estimated by the position and posture calculating portion.

2. The endoscope system according to claim 1, wherein:

the position and posture calculating portion further estimates a posture of the distal end portion of the endoscope insertion portion that includes a longitudinal direction of the distal end portion of the endoscope insertion portion; and in a case where an angle that the core line direction and the longitudinal direction of the distal end portion of the endoscope insertion portion form is equal to or less than a predetermined threshold value, the position and posture information recording portion records information regarding a position of the distal end of the endoscope insertion portion and a posture of the distal end portion of the endoscope insertion portion that is estimated by the position and posture calculating portion.

3. The endoscope system according to claim 2, further comprising:

a direction comparing portion that compares the core line direction of the luminal organ of the subject and a longitudinal direction of the distal end portion of the endoscope insertion portion; wherein:

the direction comparing portion performs a comparison between a past longitudinal direction that is based on information regarding the longitudinal direction that is recorded in the past in the position and posture information recording portion and a current longitudinal direction that is estimated by the position and posture calculating portion; and the positional information recording portion records information regarding a position and a posture of the distal end of the endoscope insertion portion in a case where an angle that the past longitudinal direction that is obtained by the direction comparing portion and the current longitudinal direction that is estimated by the position and posture calculating portion form is greater than a second predetermined threshold value.

4. The endoscope system according to claim 3, wherein the direction comparing portion performs a comparison between the core line direction and the longitudinal direction in a case where a movement distance of the distal end of the endoscope insertion portion in the luminal organ is greater than or equal to a predetermined distance interval.

5. The endoscope system according to claim 3, comprising an image pickup portion that is provided in the endoscope and is configured to pick up an image of inside of the luminal organ, and further comprising:

a direction change detecting portion configured to detect a change in a direction of an endoscopic image that is acquired by the image pickup portion;

wherein the position and posture information recording portion records information regarding a position and a posture of the distal end of the endoscope insertion portion in a case where a change that is greater than or equal to a threshold value is detected with respect to an angle formed by a direction of the endoscopic image that is detected by the direction change detecting portion and a direction of an endoscopic image that is recorded in the position and posture information recording portion.

6. The endoscope system according to claim 3, the endoscope system being capable of previously acquiring image information corresponding to the shape information, further comprising:

an image pickup portion that is provided in the endoscope and is configured to pick up an image of inside of the luminal organ;

a virtual endoscopic image generating portion configured to generate a virtual endoscopic image that is endoscopically rendered from a predetermined viewing point position based on the image information; and an image comparing portion configured to compare an endoscopic image of inside of the predetermined luminal organ that is picked up by the image pickup portion and the virtual endoscopic image;

wherein the position and posture calculating portion calculates information regarding a position and a posture of the distal end of the endoscope insertion portion based on a comparison result of the image comparing portion.

7. The endoscope system according to claim 3, further comprising:

a route data generating portion configured to, in a case where a target site is specified with respect to shape information of the subject, generate route data from an insertion starting position of the distal end of the endoscope insertion portion in the luminal organ to a target position that is in a vicinity of the target site based on the shape information and a luminal shape image of the luminal organ that is extracted by a luminal organ extracting portion; and a branch information recording portion configured to record branch information including a three-dimensional position and a branching angle of a branch point at which the luminal organ branches during the course of arriving at the target position of the route data;

wherein:

the branch information recording portion automatically determines the second predetermined threshold value in accordance with the branch information of the branch point; and the direction comparing portion performs a comparison using the second predetermined threshold value that is determined.

8. The endoscope system according to claim 7, wherein, based on a three-dimensional position of the distal end of the endoscope insertion portion at a time that a current longitudinal direction is detected by the position and posture calculating portion, the branch information recording portion automatically determines the second predetermined threshold value based on branch information of a next branch point that exists at a location that is further along a target position side than the three-dimensional position.

9. The endoscope system according to claim 2, the endoscope system being capable of previously acquiring image information corresponding to the shape information, further comprising:
- an image pickup portion that is provided in the endoscope and is configured to pick up an image of inside of the luminal organ;
- a virtual endoscopic image generating portion configured to generate a virtual endoscopic image that is endoscopically rendered from a predetermined viewing point position based on the image information; and
- an image comparing portion configured to compare an endoscopic image of inside of the luminal organ that is picked up by the image pickup portion and the virtual endoscopic image;
- wherein the position and posture calculating portion estimates information regarding a position and a posture of the distal end of the endoscope insertion portion based on a comparison result of the image comparing portion.

10. The endoscope system according to claim 9, wherein, together with the information regarding a position and a posture of the distal end of the endoscope insertion portion, the position and posture information recording portion records the virtual endoscopic image and information regarding a direction of an endoscopic image that is picked up by the image pickup portion that correspond to the position and the posture of the distal end of the endoscope insertion portion.

11. The endoscope system according to claim 9, further comprising:
- a luminal shape image generating portion configured to generate a luminal shape image of the luminal organ based on the shape information; and
- a display portion configured to, in a case where image matching by comparing the endoscopic image and the virtual endoscopic image using the image comparing portion cannot be performed within a set accuracy, superimpose information regarding a position and a posture of the distal end of the endoscope insertion portion that is recorded in the position and posture information calculating portion on the luminal shape image and display a resulting image.

\* \* \* \* \*